US008425579B1

(12) United States Patent
Edelman et al.

(10) Patent No.: US 8,425,579 B1
(45) Date of Patent: Apr. 23, 2013

(54) THERAPEUTIC KNEE BRACE FOR A CONTRAST THERAPY SYSTEM

(75) Inventors: Howard Edelman, San Francisco, CA (US); Daqing Liu, Foster City, CA (US)

(73) Assignee: VitalWear, Inc., South San Francisco, CA (US)

( * ) Notice: Subject to any disclaimer, the term of this patent is extended or adjusted under 35 U.S.C. 154(b) by 1087 days.

(21) Appl. No.: 11/538,278

(22) Filed: Oct. 3, 2006

Related U.S. Application Data

(63) Continuation-in-part of application No. 10/267,247, filed on Oct. 8, 2002, now Pat. No. 7,211,104.

(51) Int. Cl.
*A61F 7/00* (2006.01)
*A61H 1/00* (2006.01)

(52) U.S. Cl.
USPC ........... 607/104; 607/108; 607/112; 607/114; 601/34

(58) Field of Classification Search .................. 607/104, 607/108, 112, 114; 601/34
See application file for complete search history.

(56) References Cited

U.S. PATENT DOCUMENTS

| | | | |
|---|---|---|---|
| 26,663 A | 1/1860 | French | |
| 128,220 A | 6/1872 | Gardner et al. | |
| 267,435 A | 11/1882 | Leiter | |
| 301,931 A | 7/1884 | Smith et al. | |
| 430,721 A | 6/1890 | Winkler | |
| 691,270 A | 1/1902 | Jones | |
| 787,920 A | 4/1905 | Hofmann | |
| 889,964 A | 6/1908 | Powell | |
| 1,817,277 A | 8/1931 | Uhlig | |
| 2,322,449 A | 6/1943 | Johnson et al. | |
| 2,451,218 A | 10/1948 | Hengst | |
| 2,504,569 A | 4/1950 | Murphy et al. | |
| 2,518,299 A | 8/1950 | Fernandez | |
| 2,666,656 A | 1/1954 | Bruning | |
| 2,726,658 A | 12/1955 | Chessey | |
| 2,773,531 A | 12/1956 | La Verne Johnson | |
| 2,896,977 A | 7/1959 | Hansen | |
| 2,911,974 A | 11/1959 | Spence | |
| 3,132,688 A | 5/1964 | Nowak | |
| 3,140,365 A | 7/1964 | Voland | |

(Continued)

FOREIGN PATENT DOCUMENTS

DE 3343664 3/1985
DE 3410413 10/1985

(Continued)

*Primary Examiner* — Linda Dvorak
*Assistant Examiner* — Kaitlyn Smith
(74) *Attorney, Agent, or Firm* — Kang S. Lim

(57) ABSTRACT

The present invention relates to a therapeutic knee brace system including a leg brace for support, a retainer for securing the therapeutic knee brace system to a knee joint therapy site, a brace joint providing a limited range of flexion to the knee brace, and an active thermal exchange bladder coupled to a contrast therapy system for delivering a therapy fluid at a select temperature, pressure and rate. Thermal exchange bladder is removable, and the pressure may be constant or dynamic. The angle of flexion may be selected by the therapy recipient, and the range of flexion of the brace joint is configurable. The knee brace may communicate range and instant angle of flexion of the brace joint to a continuous passive motion (CPM) device, and communication may be mechanical, electronic or wireless. A knee brace coupler attaches to a CPM coupler on the CPM device to selectively couple the therapeutic knee brace system to the CPM device.

8 Claims, 31 Drawing Sheets

U.S. PATENT DOCUMENTS

| | | | | |
|---|---|---|---|---|
| 3,191,972 | A | 6/1965 | Collar | |
| 3,283,780 | A | 11/1966 | Sutton | |
| 3,284,842 | A | 11/1966 | Jennings, Jr. | |
| 3,460,801 | A | 8/1969 | Norton | |
| 3,548,819 | A | 12/1970 | Davis et al. | |
| 3,556,470 | A | 1/1971 | Ehrens | |
| 3,586,048 | A | 6/1971 | Arnold | |
| 3,612,059 | A | 10/1971 | Ersek | |
| 3,648,765 | A | 3/1972 | Starr | |
| 3,683,902 | A | 8/1972 | Artemenko et al. | |
| 3,744,555 | A | 7/1973 | Fletcher et al. | |
| 3,788,348 | A | 1/1974 | Johnson | |
| 3,869,871 | A | 3/1975 | Rybalko et al. | |
| 3,871,381 | A | 3/1975 | Roslonski | |
| 3,886,936 | A | 6/1975 | Wehrenberg | |
| 3,901,225 | A | 8/1975 | Sconce | |
| 3,916,929 | A | 11/1975 | Brown | |
| 3,993,053 | A | 11/1976 | Grossan | |
| 3,995,621 | A | 12/1976 | Fletcher et al. | |
| 4,099,522 | A | 7/1978 | Alenares | |
| 4,149,529 | A | 4/1979 | Copeland et al. | |
| 4,149,541 | A | 4/1979 | Gammons et al. | |
| 4,184,537 | A | 1/1980 | Sauder | |
| 4,196,772 | A | 4/1980 | Adamski et al. | |
| 4,273,290 | A | 6/1981 | Quinn | |
| 4,338,944 | A | 7/1982 | Arkans | |
| 4,459,468 | A | 7/1984 | Bailey | |
| 4,538,595 | A * | 9/1985 | Hajianpour | 601/33 |
| 4,552,132 | A | 11/1985 | Ruscigno | |
| 4,587,959 | A | 5/1986 | Ruderian | |
| 4,669,476 | A | 6/1987 | Gordon et al. | |
| 4,691,762 | A | 9/1987 | Elkins et al. | |
| 4,703,957 | A | 11/1987 | Blenkush | |
| 4,715,361 | A * | 12/1987 | Mauldin et al. | 601/101 |
| 4,733,692 | A | 3/1988 | Kotake et al. | |
| 4,823,651 | A | 4/1989 | England | |
| 4,825,852 | A * | 5/1989 | Genovese et al. | 601/34 |
| 4,844,072 | A | 7/1989 | French et al. | |
| 4,846,176 | A | 7/1989 | Golden | |
| 4,877,181 | A | 10/1989 | Stewart | |
| 4,910,978 | A | 3/1990 | Gordon et al. | |
| 4,913,316 | A | 4/1990 | Richter | |
| 4,930,497 | A * | 6/1990 | Saringer | 601/34 |
| 4,962,761 | A | 10/1990 | Golden | |
| 4,989,790 | A | 2/1991 | Martin et al. | |
| 5,013,013 | A | 5/1991 | Spedding | |
| 5,038,852 | A | 8/1991 | Johnson et al. | |
| 5,051,562 | A | 9/1991 | Bailey et al. | |
| 5,072,875 | A | 12/1991 | Zacoi | |
| 5,077,980 | A | 1/1992 | Weber | |
| 5,080,089 | A | 1/1992 | Mason et al. | |
| 5,086,771 | A | 2/1992 | Molloy | |
| 5,143,064 | A | 9/1992 | Cochran | |
| D331,115 | S | 11/1992 | Stout | |
| D333,350 | S | 2/1993 | Redira, Jr. | |
| 5,183,039 | A | 2/1993 | Sarian et al. | |
| 5,228,432 | A * | 7/1993 | Kaiser et al. | 601/34 |
| 5,230,335 | A | 7/1993 | Johnson, Jr. et al. | |
| 5,232,020 | A | 8/1993 | Mason et al. | |
| 5,234,166 | A | 8/1993 | Foster et al. | |
| 5,252,102 | A * | 10/1993 | Singer et al. | 623/24 |
| D344,343 | S | 2/1994 | McNew | |
| 5,314,455 | A | 5/1994 | Johnson, Jr. et al. | |
| 5,316,041 | A | 5/1994 | Ramacier, Jr. et al. | |
| 5,324,318 | A | 6/1994 | Smith | |
| 5,324,319 | A | 6/1994 | Mason et al. | |
| 5,330,519 | A | 7/1994 | Mason et al. | |
| 5,334,135 | A * | 8/1994 | Grim et al. | 602/26 |
| 5,344,436 | A | 9/1994 | Fontenot et al. | |
| 5,368,234 | A | 11/1994 | Foster et al. | |
| 5,372,608 | A | 12/1994 | Johnson | |
| 5,383,919 | A * | 1/1995 | Kelly et al. | 607/104 |
| 5,386,823 | A | 2/1995 | Chen | |
| 5,399,147 | A * | 3/1995 | Kaiser | 601/34 |
| 5,407,421 | A * | 4/1995 | Goldsmith | 602/5 |
| D358,216 | S | 5/1995 | Dye | |
| 5,411,541 | A * | 5/1995 | Bell et al. | 607/104 |
| 5,417,720 | A | 5/1995 | Mason | |
| 5,433,083 | A | 7/1995 | Kuramarohit | |
| 5,439,473 | A | 8/1995 | Jorgensen | |
| 5,441,533 | A | 8/1995 | Johnson et al. | |
| 5,449,379 | A | 9/1995 | Hadtke | |
| 5,456,701 | A | 10/1995 | Stout | |
| 5,466,250 | A | 11/1995 | Johnson, Jr. et al. | |
| 5,466,251 | A | 11/1995 | Brunson et al. | |
| 5,476,489 | A | 12/1995 | Koewler | |
| 5,486,207 | A | 1/1996 | Mahawili | |
| 5,499,766 | A | 3/1996 | Foster et al. | |
| 5,507,792 | A | 4/1996 | Mason et al. | |
| D369,866 | S | 5/1996 | Baughn | |
| 5,555,579 | A | 9/1996 | Wu | |
| 5,562,604 | A | 10/1996 | Yablon et al. | |
| 5,603,728 | A | 2/1997 | Pachys | |
| 5,617,811 | A | 4/1997 | Johnson | |
| 5,647,051 | A | 7/1997 | Neer | |
| 5,662,695 | A | 9/1997 | Mason et al. | |
| 5,668,565 | A | 9/1997 | Robinson | |
| 5,711,155 | A | 1/1998 | DeVilbiss et al. | |
| 5,711,746 | A * | 1/1998 | Carlson | 482/112 |
| RE35,744 | E | 3/1998 | Foster et al. | |
| D393,719 | S | 4/1998 | Nichols | |
| 5,738,636 | A * | 4/1998 | Saringer et al. | 601/5 |
| 5,741,220 | A | 4/1998 | Brink | |
| 5,755,275 | A | 5/1998 | Rose et al. | |
| 5,755,733 | A | 5/1998 | Morita | |
| 5,755,755 | A | 5/1998 | Panyard | |
| 5,865,841 | A | 2/1999 | Kolen et al. | |
| 5,891,188 | A | 4/1999 | Maytal | |
| 5,894,615 | A | 4/1999 | Alexander | |
| 5,904,291 | A | 5/1999 | Knapp | |
| 5,968,072 | A | 10/1999 | Hite et al. | |
| 5,980,561 | A * | 11/1999 | Kolen et al. | 607/104 |
| 6,050,297 | A | 4/2000 | Ostrowski et al. | |
| 6,117,164 | A * | 9/2000 | Gildersleeve et al. | 607/108 |
| 6,149,617 | A | 11/2000 | McNally et al. | |
| 6,270,055 | B1 | 8/2001 | Szeteli et al. | |
| 6,295,819 | B1 | 10/2001 | Mathiprakasam et al. | |
| 6,299,626 | B1 | 10/2001 | Viranyi | |
| 6,352,550 | B1 | 3/2002 | Gildersleeve et al. | |
| 6,440,159 | B1 | 8/2002 | Edwards et al. | |
| 6,551,347 | B1 * | 4/2003 | Elkins | 607/104 |
| 6,699,267 | B2 | 3/2004 | Voorhees et al. | |
| 6,827,728 | B2 | 12/2004 | Ellingboe et al. | |
| 6,872,187 | B1 * | 3/2005 | Stark et al. | 602/16 |
| 6,957,697 | B2 | 10/2005 | Chambers | |
| 7,000,682 | B2 | 2/2006 | Chambers | |
| 7,191,798 | B2 | 3/2007 | Edelman et al. | |
| 7,211,104 | B2 | 5/2007 | Edelman | |
| 2001/0018604 | A1 | 8/2001 | Elkins | |
| 2001/0039439 | A1 | 11/2001 | Elkins et al. | |
| 2002/0019657 | A1 | 2/2002 | Elkins | |
| 2002/0026226 | A1 | 2/2002 | Ein | |
| 2002/0032473 | A1 | 3/2002 | Kushnir et al. | |
| 2004/0068310 | A1 | 4/2004 | Edelman | |
| 2007/0161932 | A1 * | 7/2007 | Pick et al. | 602/5 |
| 2008/0097269 | A1 * | 4/2008 | Weinberg et al. | 602/16 |
| 2009/0112134 | A1 * | 4/2009 | Avni | 601/15 |
| 2009/0204038 | A1 * | 8/2009 | Smith et al. | 602/13 |
| 2009/0312681 | A1 * | 12/2009 | McSpadden et al. | 602/2 |
| 2011/0160625 | A1 * | 6/2011 | Yefimov | 601/5 |

FOREIGN PATENT DOCUMENTS

| | | |
|---|---|---|
| GB | 2 175 496 A | 12/1986 |
| IT | 246899 | 3/1926 |
| SU | 577-350 | 10/1977 |

\* cited by examiner

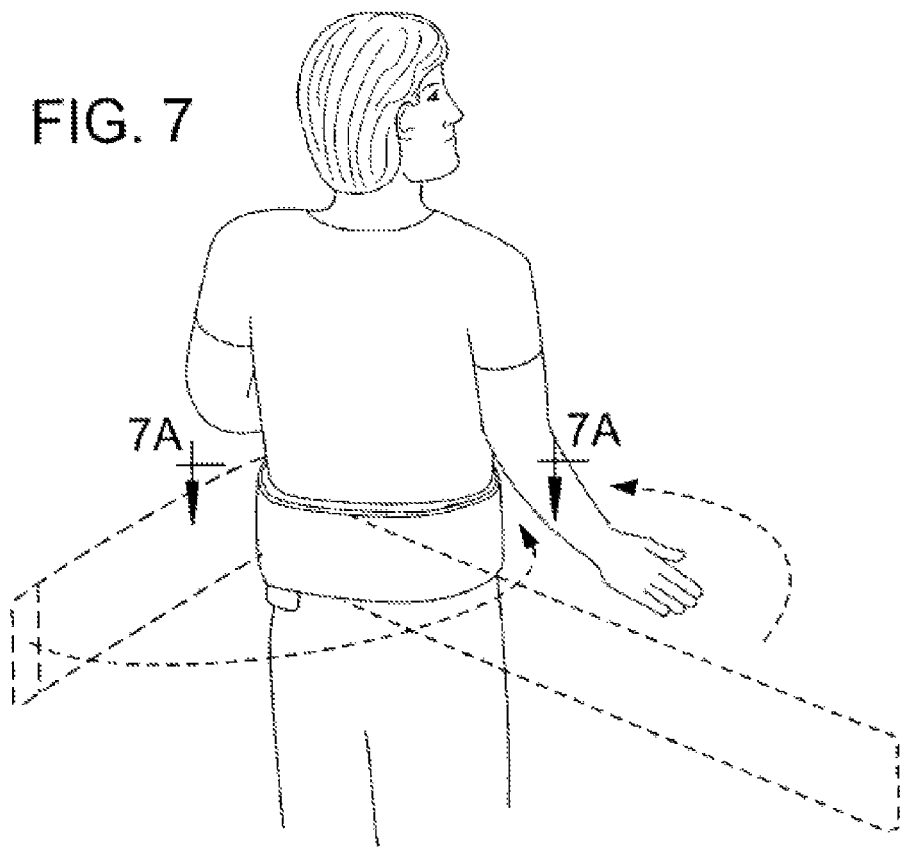

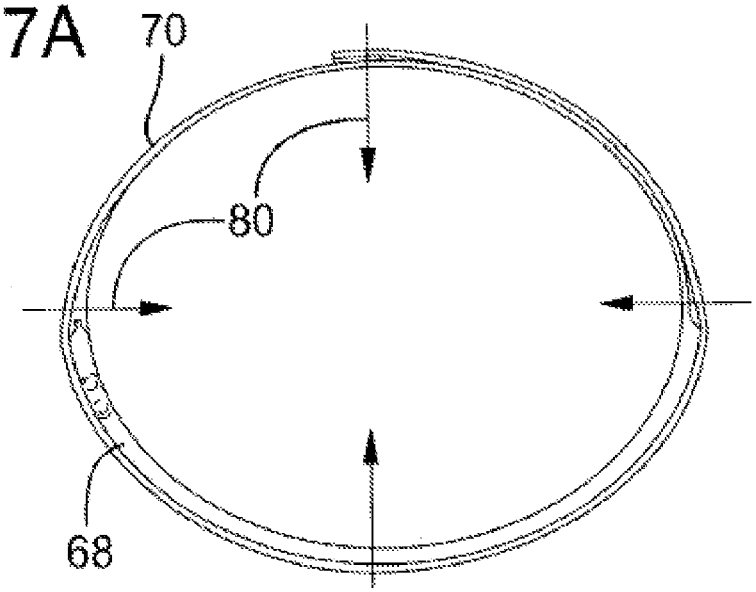

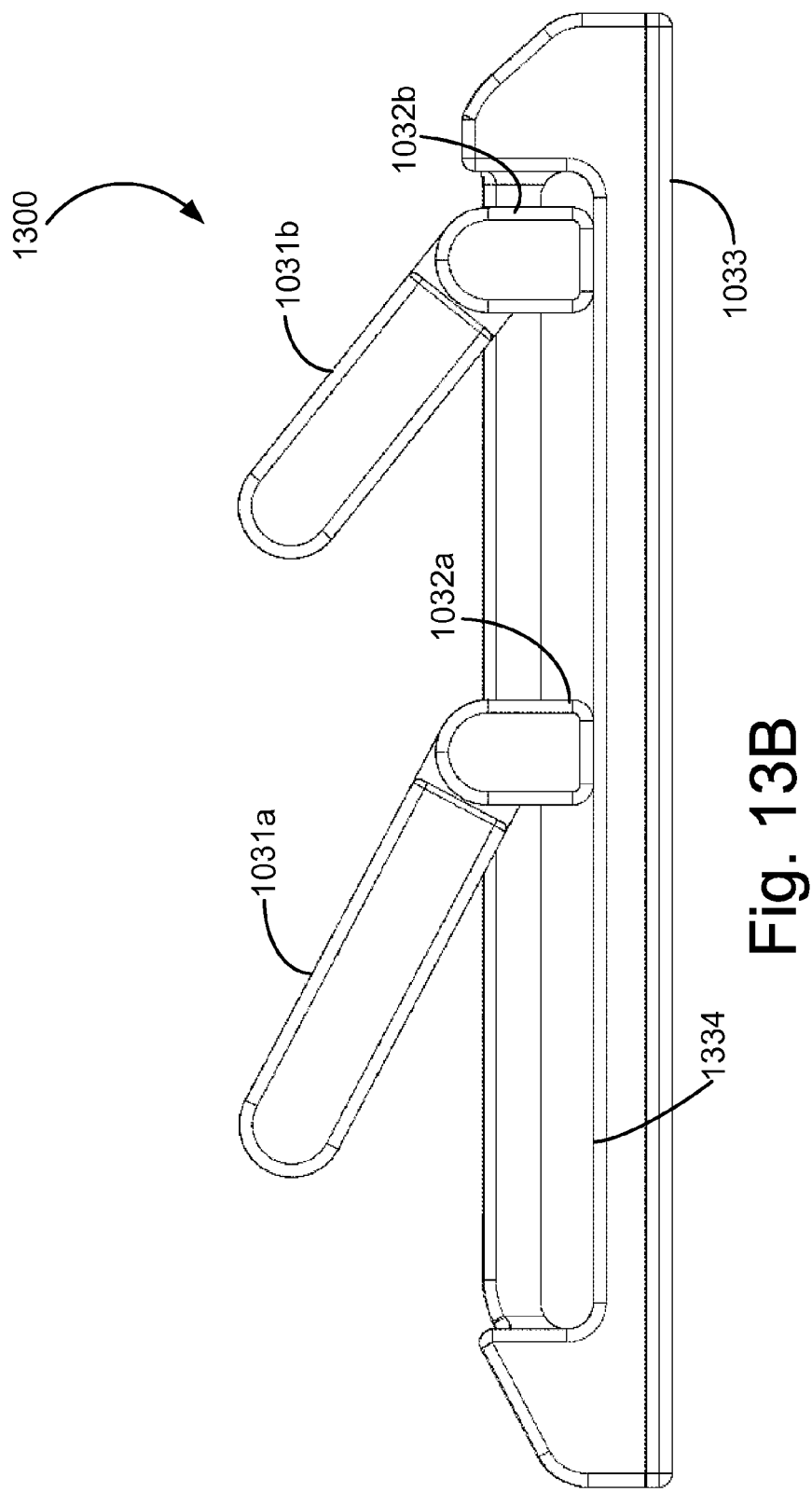

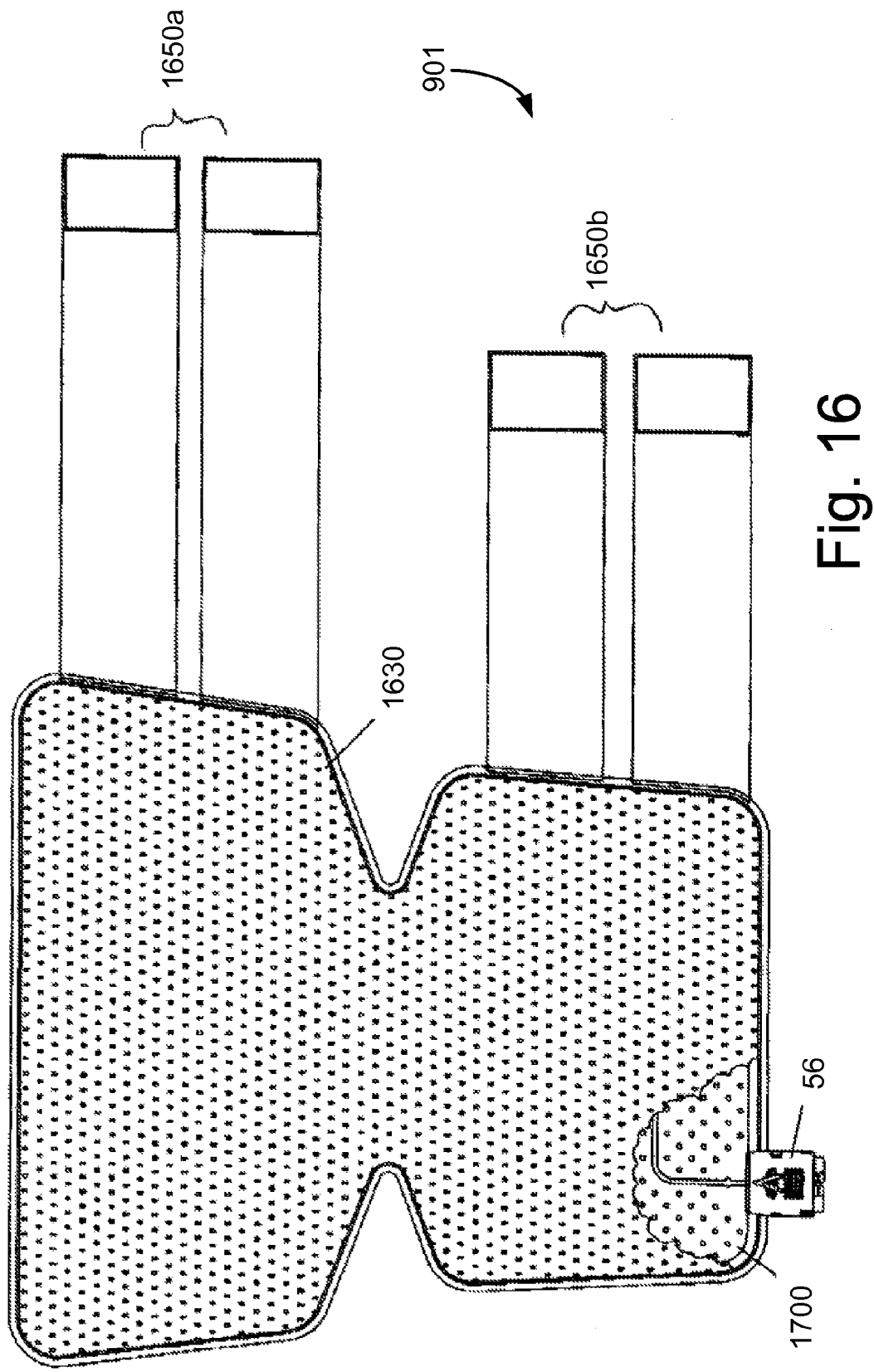

THERAPEUTIC KNEE BRACE FOR A CONTRAST THERAPY SYSTEM

CROSS REFERENCE TO RELATED APPLICATIONS

This is a continuation-in-part of co-pending U.S. application Ser. No. 10/267,247 filed on Oct. 8, 2002, entitled "Contrast Therapy System and Method", which is hereby fully incorporated by reference.

BACKGROUND OF THE INVENTION

The present invention relates to knee braces, and more particularly, to knee brace assemblies in conjunction with continuous passive motion (hereinafter "CPM"), which incorporate bladders, and which are adapted for use in a thermal or contrast therapy system, or medical thermal therapy system. The bladder element of the present invention enables the user to obtain a tightly controlled and consistent temperature or contrast therapy, along with support, pressure and/or compression therapy. Additionally, the knee brace includes an intelligent joint, capable of being configured to a range of flexion and transmitting the instant angle and the configured range of flexion to the continuous passive motion device.

Knee impairments affect over 13.5 million people in the United States in 2001. Knee impairments account for almost half of the musculoskeletal impairments in the United States. The knee is the largest joint in the body, and its exposed position makes it vulnerable to injury during activities. Knee impairments affect a person's ability to walk, crouch, climb and otherwise move freely. Additionally, knee impairments can be extremely debilitating and painful.

Knee braces are commonly utilized to alleviate pain, provide stability, increased mobility, and reduced healing time after injury, medical procedure or ailment of the knee. Knee braces may be rigid or semi-rigid, providing medial and lateral knee stability to protect the medial and lateral collateral ligaments, meniscus and joint cartilage. Adjustable hinges may be included to provide protection of the ACL and PCL ligaments. Flexion and extension stops may be included to control knee joint range of motion. Additionally, by wrapping tightly around the leg the knee brace may provide compressive therapy. Knee braces alleviate pain and allow damaged tissue to properly heal and rehabilitate.

In addition, it is often important to flex and extend therapy sites in order to provide effective therapy. A prescribed therapeutic regime may include a regimen of flexing and extending the implicated site. In addition to flexure and extension, active physical therapy may include additional holding and stretching with the assistance of a physical therapist or physician. Such additional flexing, stretching and holding at certain points within the critical or working range of motion, as well as flexing and extending through an appropriate therapeutic range of motion, may help increase the rate of rehabilitation.

In addition to active physical therapy, systems and methods of applying passive therapeutic motion have been developed. The therapeutic use of an external force to flex and extend the limb to induce motion is referred to as passive motion. The application of continuous passive motion (CPM) to a joint following a period of immobilization, injury, surgery or the like, has been shown to reduce post-operative pain, decrease the number of adhesions, decrease the amount of atrophy experienced by the surrounding and supporting muscle, promote the speed of recovery, improve the range of motion in a much shorter time, and reduce the risk of deep vein thrombosis. Depending on the nature and severity of the injury or the nature and extent of the surgical procedure performed, therapeutic treatment sessions involving continuous passive motion may be carried out on a daily basis for several days or several weeks.

Conditions commonly requiring a knee brace or CPM include, but are not limited to, postoperative rehabilitation period for total knee arthroplasty, replacement as an adjunct to on-going physical therapy, anterior cruciate ligament repair, surgical release of arthrofibrosis/adhesive capsulitis, intra-articular cartilage fractures, Chondroplasties of focal cartilage defects, osteochondritis dissecans, abrasion arthroplasty or microfracture procedure, intra-articular fracture of the knee (e.g., tibial plateau fracture repair), autologous chondrocyte transplantation, reflex sympathetic dystrophy, dupuytren's contracture and extensive tendon fibrosis. Of all the applications of CPM, the scientific evidence is perhaps strongest for its use in promoting cartilage growth. In addition, clinical studies suggest that CPM can enhance cartilage healing during the non weight bearing period following surgery for intra-articular cartilage fractures, chondroplasties of focal cartilage defects and surgical treatment of osteochondritis dissecans.

In most patients after extensive joint surgery, attempts at joint motion cause pain and as a result, the patient fails to move the joint. This allows the tissue around the joint to become stiff and for scar tissue to form resulting in a joint which has limited range of motion and often may take months of physical therapy to recovery that motion.

The concept of using CPM in conjunction with therapy is not new. A number of known devices that are designed to impose CPM on the limb and joint of a patient for such a purpose are in use in therapeutic settings. While the incorporation of CPM into therapeutic treatment is well known, the ability to effectively apply thermal therapy while the therapy site is in active or passive motion has heretofore been unknown. The use of thermal therapy may increase the effectiveness of a therapeutic regimen of motion. For instance, implicated therapy sites are often sore upon entrance into therapy. The use of heat or cold therapy may help to reduce pain and, therefore, increase the amount of time a patient may endure CPM therapy. Heat therapy may help increase blood flow to the implicated site. Heat therapy may also be used to relax joint tissue, such as ligaments and tendons, to increase range of motion in a CPM setting.

Cold therapy, on the other hand may help to reduce swelling, decrease pain, and promote healing of injured tissue. Both heat and cold therapy may help increase the effectiveness of rehabilitation. Given that there is often pain associated with CPM during the application of CPM therapy, it is important to find effective ways of reducing pain during the therapy. Key benefits of having thermal therapy during CPM are to help increase mobility with heating and to help reduce pain with cooling. Additionally, the instant contrast therapy exchange layer provides constant compression at the therapy site in flexure. Compression aids in reducing swelling and may help to stabilize the therapy site in flexure. As such, the use of contrast therapy in conjunction with CPM may provide the most effective therapy.

Traditionally, the knee brace is worn separately from the CPM device, and is removed prior CPM therapy. Removal of the knee brace prior to CPM therapy may be physically difficult, painful and time consuming. The effectiveness of a therapy is dependent on the ease in which the therapy may be applied. If it is difficult for a therapy recipient to self apply a therapy, the opportunity to receive therapy may be diminished. Furthermore, if therapies are complicated and/or uncomfortable, a therapy recipient is less likely to undergo the therapy, although it may be beneficial.

It is therefore apparent that an urgent need exists for an improved knee brace that integrates the added benefits of contrast therapy and simultaneous use with a continuous passive motion device. This assembly would be able to provide a high level of knee joint support, readily compatible with CPM therapy, and with the addition of a thermal therapy that may be very well regulated.

SUMMARY OF THE INVENTION

To achieve the foregoing and in accordance with the present invention, a Therapeutic Knee Brace System for use with a continuous passive motion device, including a thermal contrast therapy systems and methods for providing a temperature regulated fluid are provided. Such systems are useful for providing effective knee joint support with integrated contrast thermal therapy and continuous passive motion therapy.

The therapeutic knee brace system includes a leg brace to support to the knee joint, a retainer adapted to secure the therapeutic knee brace system to the therapy recipient's leg, a brace joint enabling therapeutic knee brace system to flex along the knee joint of the therapy recipient, and a knee brace coupler for coupling the therapeutic knee brace system to the continuous passive motion device.

The angle of flexion of the knee brace may be selected by the therapy recipient. The range of flexion of the brace joint may be configurable. Additionally, the knee brace communicates the angle of flexion and the range of flexion through mechanical, electrical or wireless means.

The knee brace coupler may be positive, such as a pin adapted to releasably engage into a complimentary slot on the continuous passive motion (CPM) device, or negative such as a slot adapted to releasably be engaged by a complimentary pin on the CPM device.

Additionally, the knee brace coupler is configured to selectively couple the therapeutic knee brace system with a specific CPM device, and the specific CPM device is configured to selectively couple with the therapeutic knee brace system. Such a selective ability to couple is important to ensure proper use and regulation of the knee brace in conjunction with the CPM device. Moreover, the knee brace coupler, when the knee brace is coupled with the CPM device, allows the CPM device to function, wherein the functioning includes the movement of the knee brace in passive motion, generating flexion along the brace joint when the knee brace is fully engaging the device.

Additionally, the therapeutic knee brace system may include an active thermal exchange bladder configured to fit the knee joint of the therapy recipient. The active thermal exchange bladder is coupled to a thermal contrast therapy system that delivers a thermal therapy fluid to the thermal exchange bladder. Additionally, the thermal exchange bladder may be coupled to the leg brace.

The thermal contrast therapy system includes a hot reservoir for holding a relatively hot fluid, a cold reservoir for holding a relatively cold fluid, a mixing valve for receiving a selected ratio of the hot and cold fluids from the hot and cold reservoirs to generate the therapy fluid, a pump for pumping the therapy fluid, and operable to deliver the therapy fluid with a therapy temperature determined by the selected ratio.

The thermal exchange bladder provides compression on the knee joint of the therapy recipient through pressure, regulated by the pump, within the thermal exchange bladder. The pump may cause constant or dynamic pressure within the thermal exchange bladder, for steady compression or pulsating compression, respectively, on the knee joint of the therapy recipient.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, one embodiment will now be described, by way of example, with reference to the accompanying drawings, in which:

FIG. 7 is an isometric view of a therapy pad wrapped around a therapy recipient.

FIG. 7A is a cross-sectional view of the therapy pad of FIG. 7 wrapped around the therapy recipient.

FIG. 13B is a side view of a continuous passive motion device in accordance with an embodiment of the present invention.

FIG. 16 is a top plan view of a second face of a knee thermal exchange layer adapted for use with a continuous passive motion device in accordance with an embodiment of the present invention.

DETAILED DESCRIPTION OF THE INVENTION

The present invention will now be described in detail with reference to several embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention. The features and advantages of the present invention may be better understood with reference to the drawings and discussions that follow.

Figure 17:
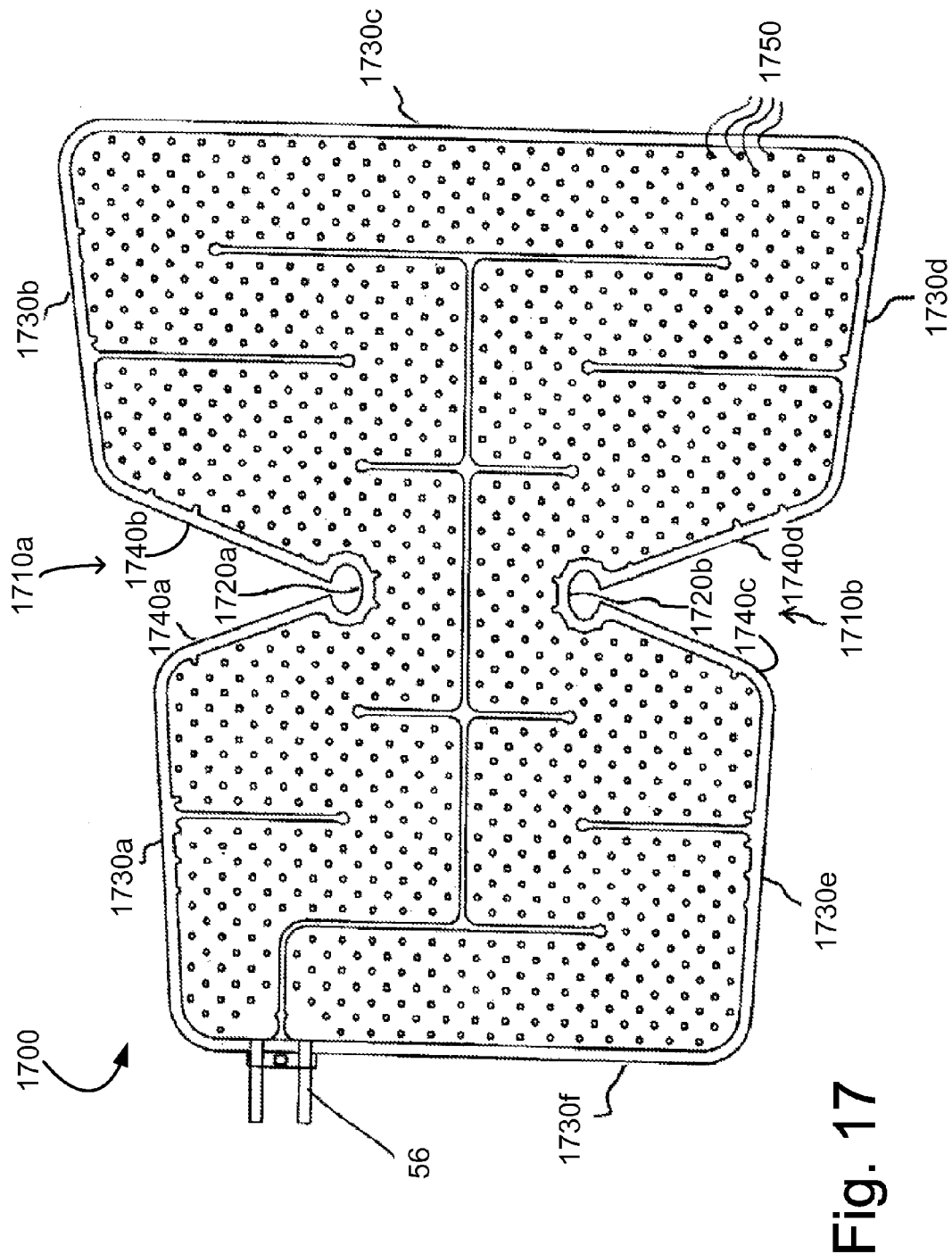
FIG. 17 is a top plan view of an active thermal exchange bladder of a knee thermal exchange layer adapted for use with a continuous passive motion device in accordance with an embodiment of the present invention.
Figure 18:
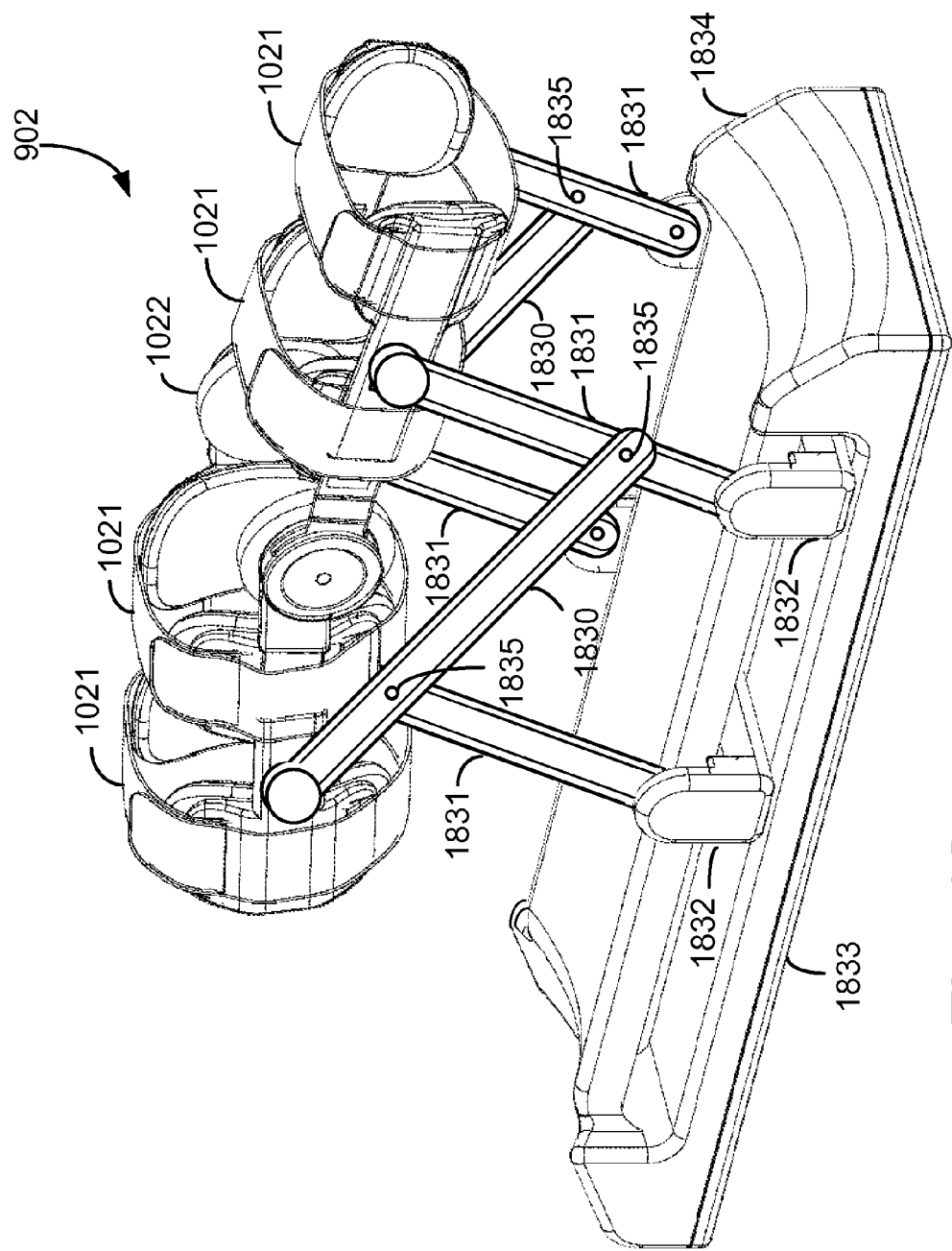
FIG. 18 is an isometric view of a therapeutic knee brace coupled with a continuous passive motion device in accordance with an embodiment of the present invention.
Figure 19:
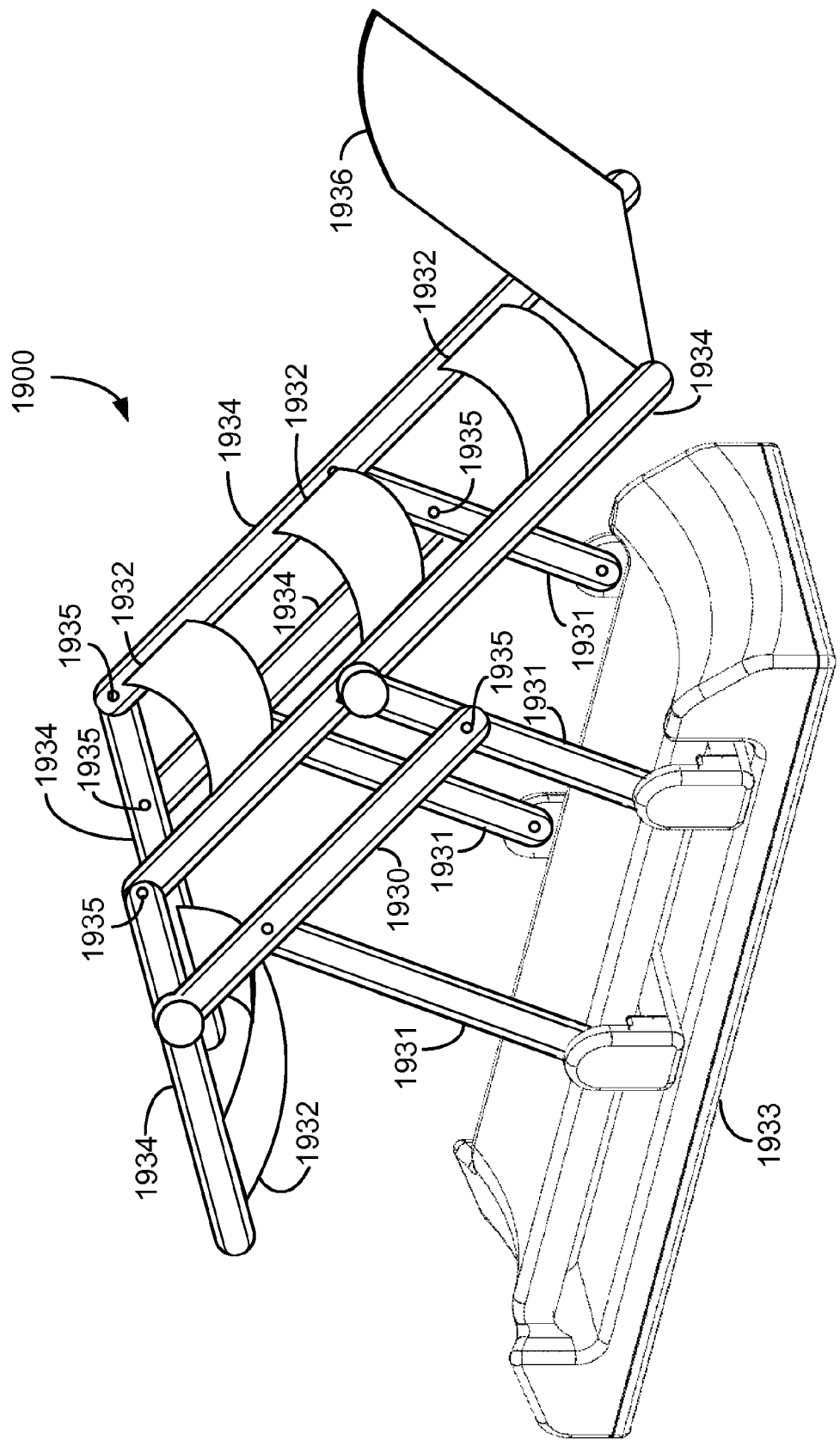
FIG. 19 is an isometric view of a continuous passive motion device in accordance with an embodiment of the present invention.
Figure 20:
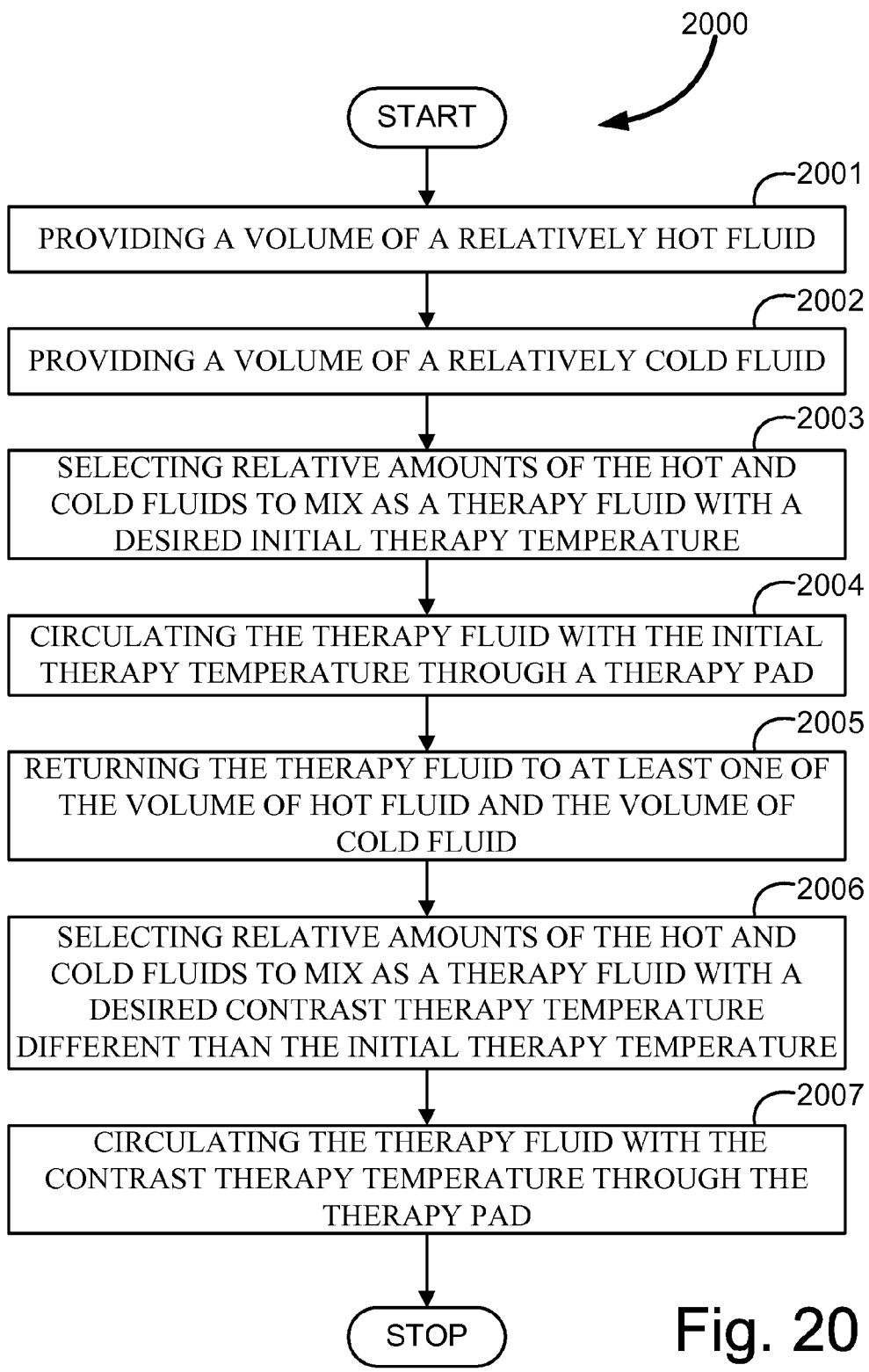
FIG. 20 is an illustration of a method for administering contrast therapy to a therapy recipient in accordance with an embodiment of the present invention.

The present invention relates to therapeutic knee brace system including thermal contrast therapy systems and a method of providing contrast therapy. Additionally, the knee brace may be used in conjunction with a Continuous Passive Motion (CPM) device for additional CPM therapy. The therapeutic use of an external force to flex and extend the limb to induce motion is referred to as passive motion. Alternatively, active motion, within the confines of the present technological art, refers to a therapeutic device requiring internal force, from the user, to flex and extend the limb. In some embodiment the CPM device may include a thermal contrast system and be separate from the knee brace. To facilitate discussion, FIGS. 1 through 8 show various views of the present contrast therapy system. FIG. 9 provides an illustration of flexion of a therapy recipient's leg when engaged in CPM therapy. FIGS. 10 through 14 show various views of the present Knee Brace and CPM Device Assembly 902. FIGS. 15 through 17 show various views of the present Thermal Exchange Layer 901 for use with the Therapeutic Knee Brace and CPM Device Assembly 902. FIGS. 18 and 19 show alternate embodiments of CPM assemblies. FIG. 20 provides an illustration of a method for providing contrast therapy to a therapy recipient.

Although useful for applying any combination of heat, cold, compression and support to a recipient for virtually any reason, the Therapeutic Knee Brace and CPM Device Assembly 902 including Thermal Contrast Therapy Systems 10 described below demonstrates particular utility for treating sore, strained, arthritic, injured, post operable, heavily exercised, and/or otherwise taxed knee joint regions. The contrast therapy system is described below in the context of providing "therapy" to a recipient, however, it should be understood that the Therapeutic Knee Brace System With Continuous Passive Motion 902 including Thermal Contrast Therapy Systems 10 are equally well suited for providing any combination of heat, cold, compression and support for what may be considered non-therapeutic purposes.

As described herein, the Contrast Therapy System 10 is capable of imparting a desired therapy temperature to a Therapy Pad 22 or in the present invention a Thermal Exchange Layer 901, which may be applied to a therapy recipient. The system is capable of shifting the therapy temperature between hot and cold temperatures very quickly, which has proven to be beneficial. The precise temperature may be set at any temperature between controlled maximum and minimum temperatures. Furthermore, the contrast therapy system may be designed as a relatively small portable unit, as shown at 30 of FIG. 1, which is both easy and inexpensive to operate. The Portable Unit 30 includes a Container 24 and a Lid Unit 28. The Lid Unit 28 includes a Dial 48 and Indicia 50 to aid in the temperature control of the contrast therapy. The Container 24 may include a Cold Reservoir 12 and an Open End 26 that the Lid Unit 28 may fit into. In some embodiment the contrast therapy system may be designed to be incorporated into the Base 1033 of the Continuous Passive Motion (CPM) Device 1300.

As described herein, the Therapeutic Knee Brace System With Continuous Passive Motion 902 is capable of imparting support to a therapy recipient, and provides a medium for the Contrast Therapy System 10. The Therapeutic Knee Brace and CPM Device Assembly 902 may include a Therapeutic Knee Brace 1200, a CPM Device 1300 and a Thermal Exchange Layer 901.

The Therapeutic Knee Brace 1200 may be secured around the leg of the therapy recipient. Therapeutic Knee Brace 1200 includes Leg Braces 1024, Padding 1025, Retainers 1021 for securing the brace to the leg, and a Brace Joint 1022. In some embodiment, the Thermal Exchange Layer 901 may be coupled to the Therapeutic Knee Brace 1200. Additional features may be incorporated into the Therapeutic Knee Brace 1200 as addressed below.

The CPM Device 1300 may be designed to couple with the Knee Brace 1200 or may be designed as a stand alone unit. The CPM Device 1300 includes of a Base 1033, an actuator, here shown as at least one Pivoting Arm 1031, and a power source to provide the passive motion. Additionally, at least one Yoke 1032 may be utilized to provide additional support and range of motion. Moreover, the Contrast Therapy System 10 may be incorporated into the Base 1033 of the CPM Device 1300. In some embodiment, the Thermal Exchange Layer 901 may be coupled to the CPM Device 1300.

The Thermal Exchange Layer 901 may be coupled to the contrast therapy system Portable Unit 30, or contrast therapy system included in the CPM Device 1300, through a Fluidic Coupling Assembly 20.

Thermal Exchange Layer 901, as seen in FIGS. 15, 16 and 17, includes an integrated Thermal Exchange Bladder 1700, seen in FIG. 17. The Thermal Exchange Layer 901 has a First Face 1630 comprised of a mesh, or other efficient thermal exchange medium, to ensure rapid transference of temperature from the Thermal Exchange Layer 901 to the therapy recipient. Additionally, the Thermal Exchange Layer 901 may utilize Adjustable Elastic Straps 1550 for securing the Thermal Exchange Layer 901 to the therapy site. Hook Material 1650 pads on the Adjustable Elastic Straps 1550 may releasably engage complimentary loop material on the Adjustable Elastic Straps 1550 surface thereby allowing for adjustable tension of the Adjustable Elastic Straps 1550.

The system is also capable of applying compressive force to a therapy recipient through Thermal Exchange Layer 901 and direct compression from the Retainers 1021, thus increasing the effectiveness of treatments and further providing internal support of knee ligaments.

Fluid Circuit

Figure 2:
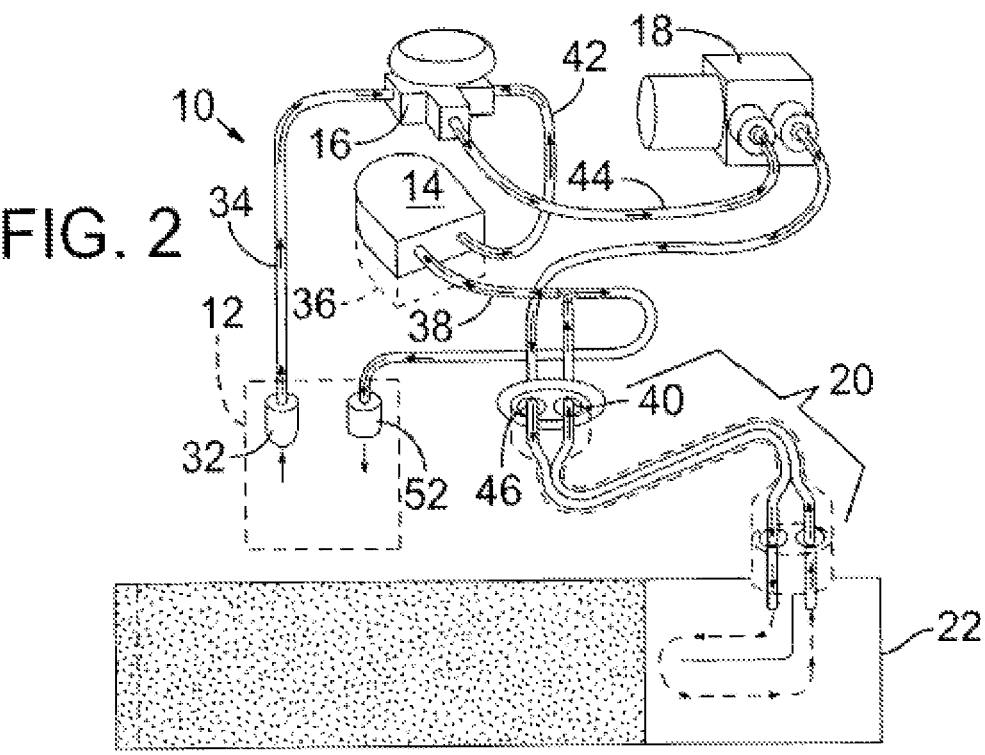
FIG. 2 is a schematic view of a fluid circuit for administering contrast therapy in accordance with an embodiment of the present invention.
Figure 3:
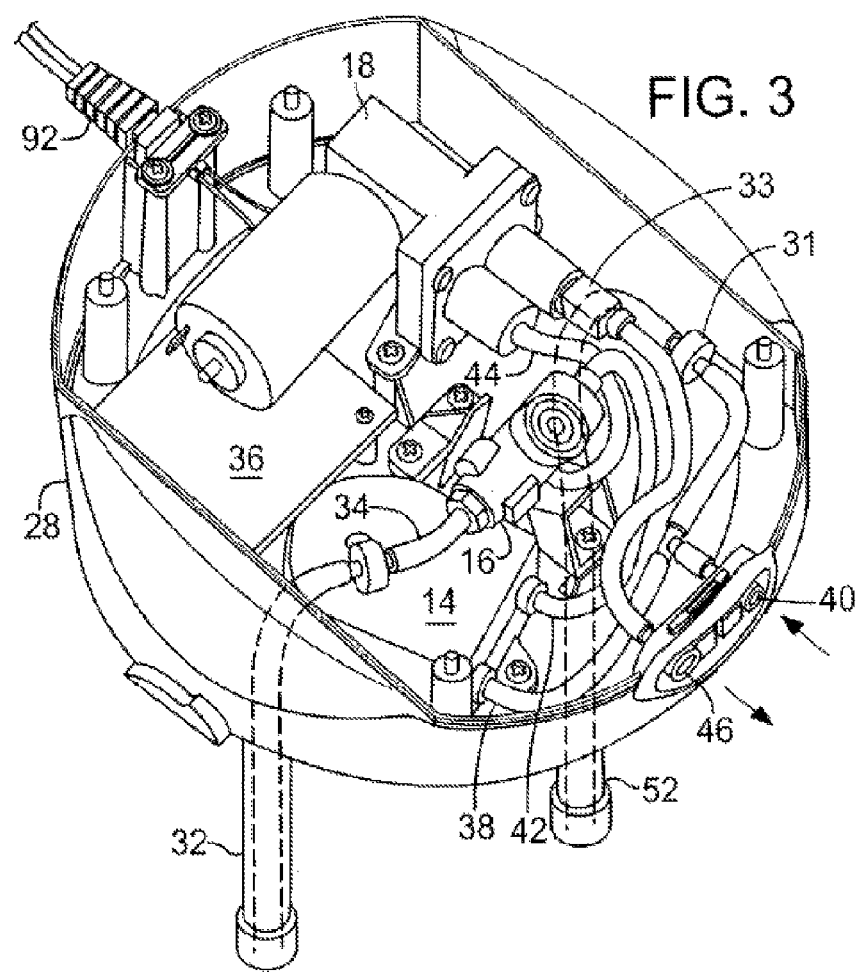
FIG. 3 is an isometric view of the fluid circuit of FIG. 2 housed within the lid portion of the contrast therapy system of FIG. 1.

FIG. 2 schematically shows a fluid circuit of the Therapeutic Knee Brace and CPM Device Assembly 902 including a Contrast Therapy System 10, and FIG. 3 shows such a circuit housed by the Lid Unit 28 of a Portable Control Unit 30. Alternatively, such a circuit may be housed within the Base 1033 of the CPM Device 1300 along with fluid reservoirs. As illustrated in FIGS. 2 and 3, the Therapeutic Knee Brace and CPM Device Assembly 902 including a Contrast Therapy System 10 includes a Cold Reservoir 12, Hot Reservoir 14, Mixing Valve 16, Pump 18, Fluidic Coupling Assembly 20, and Therapy Pad 22 which may be a Thermal Exchange Layer 901. As described in detail below, the Contrast Therapy System 10 is designed to control the temperature of a therapy fluid that circulates through the Therapy Pad 22, which includes the present Thermal Exchange Layer 901. Mixing Valve 16 selectively combines fluid received from the cold and hot reservoirs and passes the combined fluid to the Therapy Pad 22 as a therapy fluid. The Mixing Valve 16 may control the temperature of the therapy fluid, changing between hot and cold temperatures in a short period of time.

Figure 1:
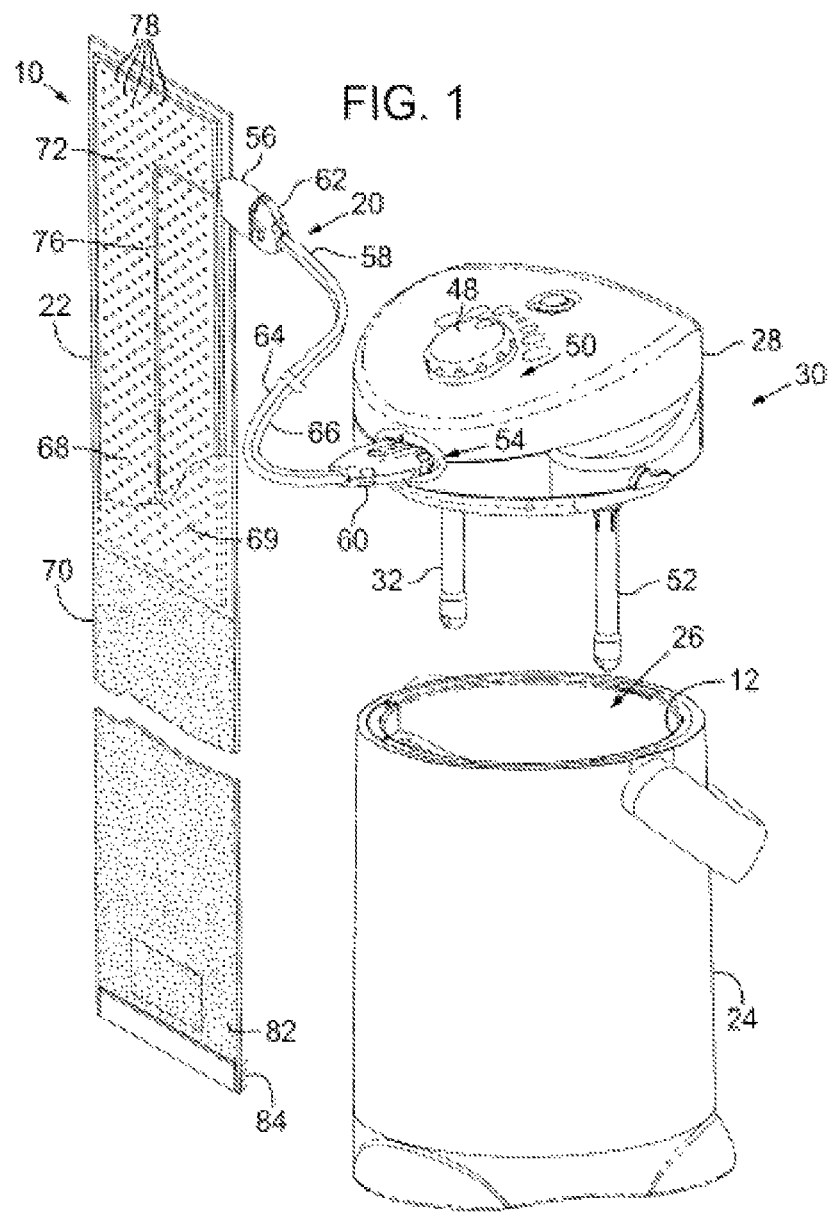
FIG. 1 is an isometric view of one embodiment of the contrast therapy system in accordance with the present invention.

Cold Reservoir 12 is designed to hold a relatively cold fluid, which may be passed to the Mixing Valve 16 and eventually to the Therapy Pad 22. As shown in FIG. 1, Cold Reservoir 12 may include the Container 24 with an Open End 26 suitable for receiving the Lid Unit 28. The Container 24 and the Lid Unit 28 may be components of the Portable Control Unit 30. The Cold Reservoir 12 may be dimensioned to hold virtually any volume of fluid, and is shown as a 4.2 Liter receptacle. Of course, smaller Cold Reservoirs 12 may be used, for example, when increased portability is desired, and larger Cold Reservoirs 12 may be used when, for example, increased capacity is desired. Alternatively, the Cold Reservoirs 12 and additional components of the fluid circuit may be housed within the CPM Device 1300 Base 1033.

The temperature of the Cold Reservoir 12 may be controlled by various mechanisms. In some embodiments, the Cold Reservoir 12 is adapted to receive ice that may melt in the Cold Reservoir 12, and thus decrease the temperature of the fluid in the Cold Reservoir 12. As shown in FIG. 1, Container 24 has a large Open End 26 that is suitable for easily receiving ice. In some embodiments, the Cold Reservoir 12 may include a cooler for cooling the fluid held in the Cold Reservoir 12. Such a cooler may include a compressor and a refrigerant, or similar cooling mechanism. It is within the scope of the invention, however, to use virtually any other suitable method for cooling the fluid held in Cold Reservoir 12. The Cold Reservoir 12 may include insulation to limit heat transfer between the fluid held by the Cold Reservoir 12 and the external environment.

The minimum temperature of the fluid in Cold Reservoir 12 is usually limited to approximately 32 to 45 degrees Fahrenheit, although such a limitation is not necessary. In particular, it has been found that a temperature of about 32 to 45 degrees Fahrenheit is an appropriate minimum temperature. Although water is usually used as the fluid, it is within the scope of the invention to use other suitable fluids. Such fluids may be selected for particular applications based on their specific heat, viscosity, freezing point, etc.

The Contrast Therapy System 10 may include an Intake 32 for drawing fluid from the Cold Reservoir 12. The drawn fluid may pass through a Fluid Path 34 between Cold Reservoir 12 and Mixing Valve 16, as is schematically shown in FIG. 1. Fluid Path 34, as well as other Fluid Paths described herein, may utilize ⅛ inch flexible tubing, or may alternatively implement another suitable fluid transport mechanism. For example, some or all of the Fluid Paths 34 may alternatively be defined by inflexible fluid conduits. The Fluid Path 34, or other fluid channels such as Intake 32, may include filters, flow restrictors, and/or check valves. Filters may help prevent flow blockages resulting from jammed ice or other substances, and check valves may be used to prevent backflow in the system. The rate of fluid flow may be at least partially controlled by flow restrictors.

Hot Reservoir 14 is designed to hold a relatively hot fluid, which may be passed to the Mixing Valve 16 and eventually to the Therapy Pad 22. Fluid in the Hot Reservoir 14 may be heated by a Heater 36, which may be positioned adjacent the Hot Reservoir 14, or may be incorporated into the Hot Reservoir 14. The Hot Reservoir 14 may be dimensioned to hold virtually any volume of fluid, and is shown dimensioned to hold a volume of approximately 20 to 30 cubic centimeters. It should be understood that the Hot Reservoir 14 may be smaller or larger, depending on the desired use and the other components of the contrast therapy system. Additionally, the Hot Reservoir 14 may be insulated to prevent heat loss from the Hot Reservoir 14 fluid to the external environment.

Heater 36 may be configured so as to achieve a suitable balance of power consumption and heat generation. It has been found that a heater of approximately 280 Watts is appropriate for heating a volume of approximately 20 to 30 cubic centimeters under normal conditions. It should be understood that more powerful and less powerful Heaters 36 may be used. Similarly, more than one heater or type of heater may be used.

The flow rate of fluid through the Hot Reservoir 14 may correspond to the temperature of treatment being applied, with greater flow rates occurring during hotter treatments. During some hot treatments, Heater 36 may have limited time to increase the temperature of the fluid because the fluid quickly passes through the Hot Reservoir 14, and thus, the heater should be powered so as to increase the temperature a desired amount within that constrained timeframe. However, the Heater 36 does not need to completely heat the fluid from a minimum temperature to a maximum temperature in such a timeframe, although it is within the scope of the invention to do so. The Hot Reservoir 14 receives fluid from the Therapy Pad 22, and when a hot treatment is being applied, the return fluid may already be partially heated, decreasing the magnitude of heating required from Heater 36. Thus, the net temperature of the fluid may incrementally increase as it repeatedly circulates through the Hot Reservoir 14. Nevertheless, a more powerful heater may increase the rate fluid increases temperature in the Hot Reservoir 14 and/or the maximum temperature of the fluid, thus decreasing the time required to change from a cold treatment to a hot treatment. The maximum temperature of the fluid in Hot Reservoir 14 is usually limited to approximately 100 to 110 degrees Fahrenheit, although such a limitation is not required. In particular, it has been found that a temperature of about 105 degrees Fahrenheit is appropriate.

As illustrated in FIGS. 2 and 3, Hot Reservoir 14 receives fluid via a Fluid Path 38 coming from a Bulkhead Input 40. As described below, Bulkhead Input 40 receives fluid returning from the Therapy Pad 22. The returning fluid may be directed so that fluid may go to at least one of the Hot Reservoir 14, via Fluid Path 38, and the Cold Reservoir 12, via a Return 42. In some embodiments, the Hot Reservoir 14 may be housed within Lid Unit 28, which may be securely fit to Open End 26 of Container 24. Heater 36 may be controlled by an internal control system, external control system, or no control system whatsoever. If present, a control system may regulate the maximum temperature of fluid in the Hot Reservoir 14, for example. Such a control system may also be designed to maximize heating efficiency to limit energy requirements.

Contrast Therapy System 10 may include a Power Supply, such as 92 of FIG. 3, for providing power to various components of the system, such as a heater, cooler, pump, thermostat, display, etc. In some embodiments, the power supply may provide alternating current, while in other embodiments, the power supply may provide direct current. Some embodiments may be configured to operate with either AC or DC power. For example, the contrast therapy system may include a DC heater and pump designed to draw power from either a battery or an electrical outlet via an AC/DC converter. Batteries used to power the contrast therapy system may be externally connected to the system, and/or housed within the system. The contrast therapy system may be powered from alternative power sources as well.

Mixing Valve

Spinal Column Brace Including Contrast Therapy System 10 includes the Mixing Valve 16 for receiving a selected ratio of the hot and cold fluids from the Hot Reservoir 14 and Cold Reservoir 12. The Mixing Valve 16 is operable to deliver a therapy fluid with a therapy temperature that is determined by the selected ratio. In other words, Mixing Valve 16 may adjustably control the amount of hot fluid from the Hot Reservoir 14 and the amount of cold fluid from the Cold Reservoir 12 that mix together. The ratio may be 100% hot fluid from the Hot Reservoir 14, in which case the resulting therapy fluid would have a therapy temperature substantially equal to the temperature of fluid leaving the Hot Reservoir 14 (maximum temperature). The ratio may alternatively be 100% cold fluid from the Cold Reservoir 12, in which case the resulting therapy fluid would have a therapy temperature substantially equal to the temperature of fluid leaving the Cold Reservoir 12 (minimum temperature). Any temperature in between the maximum and minimum temperature may be achieved by adjusting the ratio.

The mixing valve is linked to the Cold Reservoir 12 and the Hot Reservoir 14 by respective Fluid Paths 34 and 42. In some embodiments, one or both of Fluid Paths 34 and 42 may include a pump, although no pump is required. The Mixing Valve 16 outputs therapy fluid to a Fluid Path 44 that leads to the Bulkhead Output 46, and eventually to the Therapy Pad 22. A Pump 18 may be included between the Mixing Valve 16 and the Therapy Pad 22, as shown in FIGS. 2 and 3 and described below. As with the other Fluid Paths of the contrast therapy system, these Fluid Paths may include flow restrictors, check valves, filters, over-pressure switches, and/or other components. For example, Check Valve 31 and Over Pressure Switch 33 are illustrated in FIG. 3. The flow paths may include flexible rubber tubing that is approximately ⅛ inch in diameter.

As shown in FIG. 1, the Mixing Valve 16 may be controlled by a Dial 48 that adjusts the ratio of hot and cold fluids delivered from the mixing valve. The Dial 48 may be associated with Indicia 50 that indicate a relative magnitude of a desired therapy temperature. For example, Indicia 50 may include a series of icons representing relative temperatures. A large red dot may represent the hottest therapy temperature, with red dots decreasing in size representing decreasing temperatures. Similarly, a large blue dot may represent the coldest therapy temperature, with blue dots decreasing in size representing increasing temperatures. The Dial 48 positioned to point to the large red dot may correspond to a mixing valve position that yields a ratio of 100% hot fluid. As the Dial 48 is turned through the progressively smaller red dots, and then through the progressively larger blue dots, the ratio may yield a therapy fluid with a continually increasing percentage of cold fluid.

In some embodiments, the Contrast Therapy System 10 may include a thermostat that automatically selects the ratio of hot and cold fluids delivered from the Mixing Valve 16. For example, the thermostat may be designed to receive manual input of a desired therapy temperature, and adjust the mixing valve to yield a therapy fluid with that temperature. Accordingly, the thermostat may include a temperature measuring device (not shown), such as a thermistor, thermometer, thermocouple, etc. The temperature measuring device may monitor the temperature of the therapy fluid as the thermostat adjusts the mixing valve to yield the desired therapy temperature. The temperature measuring device may cooperate with a temperature display to present the temperature of the therapy fluid. The thermostat may be programmable to automatically change the therapy temperature at a desired time or event by adjusting the ratio of hot and cold fluids delivered from the mixing valve. For example, the thermostat may be programmed to provide alternating hot therapies that last for five minutes at 105 degrees Fahrenheit and cold therapies that last for 5 minutes at 40 degrees Fahrenheit. It should be understood that the thermostat may be programmed for therapies of different durations and/or temperatures.

As shown in FIGS. 2 and 3, the Contrast Therapy System 10 may include a Pump 18 for circulating fluid through the system. As illustrated, the Pump 18 interposes the Mixing Valve 16 and the Bulkhead Output 46, although the Pump 18 may be positioned elsewhere. Similarly, more than one pump may be utilized. As is shown, the Pump 18 may be integrated into the Lid Unit 24 of the Portable Control Unit 30, however in some embodiment the Pump 18 may be integrated into the Base 1033 of the CPM Device 1300. The Pump 18 may be powered according to the desired application, and a 4 Watt pump capable of pumping 300 cubic centimeters of fluid per minute has been found to be suitable. The Pump 18 may be a reciprocating pump, a rotary pump, or virtually any other suitable pump.

In some embodiments, the Pump 18 may be configured to pulse the therapy fluid through the Therapy Pad 22, or in the present instance the Thermal Exchange Layer 901. Such a pulsing action may be translated into a therapeutic massage via the Therapy Pad 22. As the pulsing fluid circulates through the Therapy Pad 22, the Therapy Pad 22 may vibrate. Pumps designed to pulse fluid may be further enabled to adjust the relative magnitude of the pulsing to correspond to different intensities of therapeutic massages. The relative intensity may be automatically, or manually, coordinated to correspond to a particular temperature of treatment. For example, a vigorous massage may be applied during a hot treatment while a milder massage is applied during a subsequent cold treatment.

Fluidic Coupling Assembly

Figure 4:
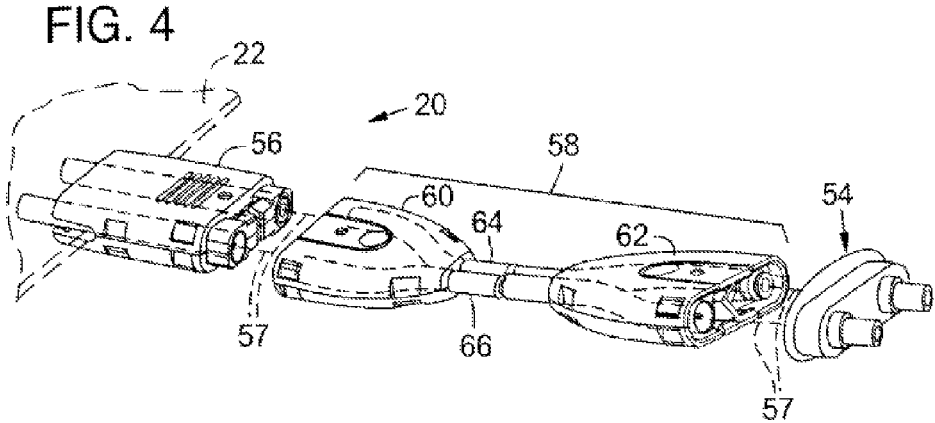
FIG. 4 is an isometric view of a fluidic coupling assembly in accordance with an embodiment of the present invention.

Therapeutic Knee Brace System With Continuous Passive Motion 902 including Contrast Therapy System 10 may include the Fluidic Coupling Assembly 20 to selectively couple and decouple the Portable Control Unit 30 and the Therapy Pad 22 or, in the present invention, the Thermal Exchange Layer 901. As shown in FIG. 4, the Fluidic Coupling Assembly 20 usually includes a Bulkhead 54, which is in fluid communication with the Mixing Valve 16, a wrap Connector 56 in fluid communication with the Thermal Exchange Bladder 1700, and a Reversible Tubing Assembly 58 for linking the Bulkhead 54 to the Connector 56. The Reversible Tubing Assembly 58 includes a First Tube-Set Connector 60 and a Second Tube-Set Connector 62 that are functionally equivalent to one another. Of course the First Tube-Set Connector 60 and the Second Tube-Set Connector 62 may be designed to differ from one another to limit connectivity as desired. First Tube-Set Connector 60 and Second Tube-Set Connector 62 are linked by Fluid Paths 64 and 66.

Bulkhead 54, First Tube-Set Connector 60, Second Tube-Set Connector 62, and Connector 56 each include one male valve and one female valve, which are configured to mate with a corresponding female and male valve, for example, as shown by dotted lines 40 in FIG. 4. The Bulkhead 54 and the Connector 56 are each configured to releasably receive either the First Tube-Set Connector 60 or the Second Tube-Set Connector 62. Therefore, Tubing Assembly 58 is completely reversible. For example, the Bulkhead 54 and the First Tube-Set Connector 60 may be coupled so that the Bulkhead's 54 male valve mates with the First Tube-Set Connector's 60 female valve, and the Bulkhead's 54 female valve mates with the First Tube-Set Connector's 60 male valve. Likewise, the Connector 56 and the Second Tube-Set Connector 62 may be coupled so that the bladder Connector's 56 male valve mates with the Second Tube-Set Connector's 62 female valve, and the bladder Connector's 56 female valve mates with the Second Tube-Set Connector's 62 male valve. Because the tubing assembly is reversible, the above described connection may be reversed. For example, if the First Tube-Set Connector 60 is connected to the Bulkhead 54, the Second Tube-Set Connector 62 is available for connection to the Connector 56, but if the Second Tube-Set Connector 62 is connected to the Bulkhead 54, the First Tube-Set Connector 60 is available for connection to the bladder Connector 56. In either case, such arrangements permit fluid to flow from the Portable Control Unit 30 to the Thermal Exchange Bladder 1700, and then return back to the Portable Control Unit 30.

The male and female valves of each of the above described components are equally spaced from one another. Therefore, male and female valves from one component may align with female and male valves from a corresponding component. Furthermore, Bulkhead 54 is complementarily configured relative to both the First and Second Tube-Set Connectors 60, 62 to facilitate securing either the First Tube-Set Connector 60 or the Second Tube-Set Connector 62 to the Bulkhead 54. Similarly, either the First Tube-Set Connector 60 or the Second Tube-Set Connector 62 may be secured to the bladder Connector 56. The male and female valves are designed to prevent fluid flow unless they are mated with one another, thus limiting leakage when disconnecting the Reversible Tubing Assembly 58 from the Portable Control Unit 30 and/or the Thermal Exchange Layer 901.

The configuration of the Fluidic Coupling Assembly 20 facilitates easy connection and disconnection of a plurality of Portable Control Units 30, Tubing Assemblies 58, Thermal Exchange Layers 901 and/or other thermal Therapy Pads 22. For example, the same Portable Control Unit 30 may be used with a variety of different Therapy Pads 22, which may be individually configured to treat different areas of a recipient's body. Similarly, Thermal Exchange Layer 901 incorporated in a Therapeutic Knee Brace System With Continuous Passive Motion 902 may be used with a variety of different Portable Control Units 30, for example, when a recipient moves from one therapy location to another. The Fluidic Coupling Assembly 20 facilitates quick and easy coupling and decoupling, and the leak reducing male and female valves help limit spillage during such coupling and decoupling.

Therapy Pad

Figure 5:
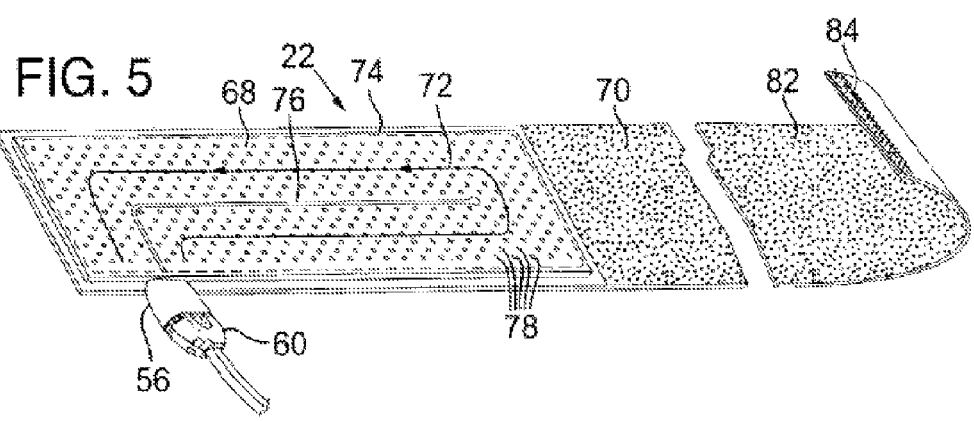
FIG. 5 is an isometric view of a contrast therapy pad in accordance with an embodiment of the present invention.

FIG. 5 shows Therapy Pad 22 apart from the remainder of the contrast therapy system. As described above, the Therapy Pad 22 may be easily coupled and decoupled from the Reversible Tubing Assembly 58, which allows various different Therapy Pads 22 to be used with the same control unit. Each Therapy Pad 22 is designed to receive therapy fluid from the mixing valve, such as through the fluidic coupling assembly, and return the therapy fluid to at least one of the hot reservoir and the cold reservoir (as shown schematically in FIG. 2). The Therapy Pad 22 returns fluid to the control unit, and the returned fluid may be recirculated. Depending on the type of therapy being applied, returned fluid may be heated and/or cooled at the control unit. The contrast therapy system may include a return valve that selectively directs return fluid to the hot reservoir and/or the cold reservoir, or the return fluid may be allowed to naturally flow to the lower pressure region.

Figure 6:
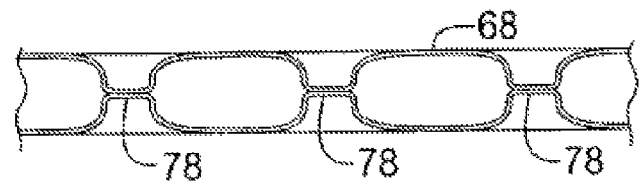
FIG. 6 is a cross-sectional view of a portion of the contrast therapy pad of FIG. 5.

In some embodiments, the Therapy Pad 22 includes an active Thermal Exchange Bladder 68 and an Elastic Wrap 70 that is connected to the Thermal Exchange Bladder 68. The Thermal Exchange Bladder 68 may include a flexible membrane of opposing faces that are welded together to define a channel system for directing the flow of therapy fluid along a desired Fluid Path 72 within the Thermal Exchange Bladder 68. For example, the faces are usually welded along a common Outer Perimeter 76, sealing the faces together. A division weld 76 may direct fluid through a substantial portion of the pad before returning to the control unit. The Thermal Exchange Bladder 68 may also include a plurality of Intermittent Welds 78, that limit inflation of the bladder, as shown in FIG. 6, which is a cross-sectional view of a portion of the exchange bladder.

The Thermal Exchange Bladder 68 facilitates thermal exchange between a therapy site and the therapy fluid. For example, when a cold therapy is administered, heat from a recipient's body may heat the therapy fluid, which in turn cools the therapy site. Similarly, when a hot therapy is administered, the therapy fluid may transfer heat to the therapy site. The therapy may be enhanced by moistening the bladder to provide a moist therapy. Furthermore, the fluid may also be pulsed through the bladder, adding a therapeutic massage aspect to the treatment.

In the illustrated embodiment, Therapy Pad 22 is dimensioned to hold approximately 26 cubic centimeters of fluid.

However, the volume of the Therapy Pad 22 may be controlled by changing the size of the Therapy Pad 22, and/or the amount of inflation the intermittent welds allow. Furthermore, the Therapy Pad 22 may be constructed from an at least partially elastic material, such as urethane, which may permit the volume to change in response to the pressure of fluid within the bladder. In some embodiments, the bladder may include a less elastic material that helps prevent stretching, such as a vinyl/urethane blend.

As shown in FIG. 5, fluid may enter the bladder at bladder Connector 56, flow around the division weld and the Intermittent Welds 78, and leave the bladder at the bladder Connector 56. It is within the scope of the invention to reconfigure the bladder to accommodate different flow paths. For example, the division weld, or plural division welds, may be used to direct the fluid through a series of switchbacks before returning to the output of the bladder Connector 56. Small breaks may be included in the division weld to permit alternative flow paths if a primary flow path is blocked.

Elastic Wrap 70 is shown connected to the Thermal Exchange Bladder 68. The Elastic Wrap 70 may be configured to adjustably wrap around the Thermal Exchange Bladder 68 and compress the Thermal Exchange Bladder 68 around a therapy site. Compression helps induce contact of the bladder with the therapy site, which may promote efficient and even thermal transfer. Furthermore, the wrap is a compressive element in and of itself. When used in conjunction with the bladder, it keeps the bladder in contact with the therapy site, and it may also help reduce swelling through its own inherent compressibility. The wrap is continuously adjustable, meaning it may be repeatedly tightened and loosened to various levels of compression, as shown in FIG. 7. The wrap may be used in tandem with the bladder to wrap a therapy site in a variety of ways, thus providing extreme flexibility in the types of treatments that may be administered to a wide range of different therapy sites.

Wrap 70 is elastic; it may be stretched and naturally return to an unstretched disposition. When stretched, the wrap is at an increased tension, which may be used to compress a Therapy Pad 22 around a therapy site, as shown in FIG. 7A. Force vectors 80 schematically represent the compressive force resulting from the wrap. The magnitude of the compressive force may be selected by adjusting the amount the wrap is stretched. As the wrap is increasingly stretched around a therapy site, the compressive force the wrap applies increases. Similarly, the wrap may be loosened, decreasing the magnitude of the compressive force. The amount of elasticity a particular wrap has may be selected according to a desired application, or range of applications. In some embodiments, the wraps are designed to stretch to approximately 150%-200% of their unstretched length, however less elastic and more Elastic Wraps 70 may be used. The wraps may be variously sized, and are usually at least as long as their corresponding bladder when unstretched. As illustrated in FIG. 5, the unstretched wrap is six times as long (54 inches) as the bladder (18 inches). Because of the elastic configuration of the wrap, wrapping techniques known to physical therapists, physical trainers, and sports physicians may be used in conjunction with the Therapy Pad 22 to achieve a wide variety of therapeutic benefits.

As shown in FIG. 5, Elastic Wrap 70 is permanently connected to Thermal Exchange Bladder 68. The wrap may be connected by stitching, an adhesive, and/or another suitable fastener. In some embodiments, the bladder is connected to the wrap via an optional mesh envelope, shown in dashed lines at 69. In such embodiments, the envelope may be permanently connected to the wrap, and the bladder may be selectively positioned within the mesh envelope. The mesh envelope may include a fastening face configured to selectively fasten with a complimentary fastener of the wrap. The wrap may alternatively be removably connected to the bladder, such as by hook and loop connectors. By permanently connecting the wrap to the bladder, such as by stitching or configuring an envelope to securely hold the bladder relative to the wrap, the wrap and the bladder may cooperate to provide a compressive force, as described herein. Furthermore, the combination has proven to be much easier to apply than separated Therapy Pads and wraps, and thus is more versatile.

The wrap usually includes a surface of loops 82 that are adapted to detachably receive complementary hooks 84. The hooks and loops are positioned, so that the hooks may engage the loops when the wrap is wrapped around a therapy site, as shown in FIGS. 7 and 7A. The wrap may be adjusted to a desired tension and a corresponding level of compressive force that may be fixed by engaging the hooks and the loops together. The hooks and loops may subsequently be disengaged, so that the tension may be adjusted, for instance, and reengaged at will. In some embodiments, a wrap lock may alternatively be used to secure the wrap.

In some embodiments, the Therapy Pads 22 may be constructed with disposable materials. For example, pads configured for a single use may be constructed from disposable materials, which are usually less expensive than reusable materials. Disposable Therapy Pads 22 may be particularly useful in emergency, trauma, or post surgery situations, in which a therapy recipient may bleed onto the Therapy Pad 22. The ability to control the temperature of the Therapy Pad 22, either reusable or disposable, may increase the pad's effectiveness as a wound dressing. Disposable materials may include less resilient versions of reusable materials and/or completely different materials. In some embodiments, disposable materials may include apertured, breathable, elastomeric and/or embossed films, as well as nonwoven laminates. Wraps may alternatively be configured to be washable, such as by a laundry machine, and therefore may be sanitarily reused.

Figure 8:
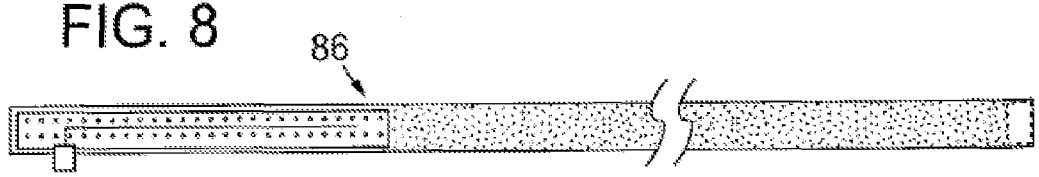
FIG. 8 is a plan view of a contrast therapy pad in accordance with an embodiment of the present invention.

The Thermal Exchange Bladder 68 may be sized and shaped according to a particular range of applications. For example, a 6 inch by 18 inch bladder (as shown at 22 in FIG. 5) may be useful in treating backs, legs, arms, shoulders, and other therapy sites. Although the versatile configuration of Therapy Pad 22 may be used for virtually any therapy site, other Therapy Pads 22 may be configured to even better accommodate particular therapy sites. For example, a 2 inch by 18 inch Bladder 86, as shown in FIG. 8, may be particularly useful for treating smaller therapy sites, such as hands, wrists, feet, ankles, etc. Similarly, a shoulder Therapy Pad 22 may be designed to intimately engage a shoulder therapy site, thus providing comfortable and improved treatment. A jaw Therapy Pad 22, which is useful in treating the facial area, may be designed to comfortably wrap around a head, while positioning a bladder in contact with at least one side of a jaw. It should be understood that the above Therapy Pads are provided as examples, and other Therapy Pads may also be used. Furthermore, each Therapy Pad 22 may include a suitable Elastic Wrap 70 and/or other fastening mechanism.

The therapy system may be used to treat a wide range of conditions, including injured muscles, bones, joints, tendons, ligaments etc. Furthermore, other conditions may be treated, such as mastitis or breasts that are sore from menstruation. The therapy system may also be used as a preventative remedy, for example the therapy system may be used during child birth to help alleviate discomfort during labor as well as help minimize resulting soreness and/or discomfort. For example, providing a cold treatment to a recipient's back during child birth may help cool the recipient, thus alleviating immediate discomfort, as well as subsequent soreness.

Therapeutic Knee Brace and Continuous Passive Motion Device Assembly

Figure 9A:
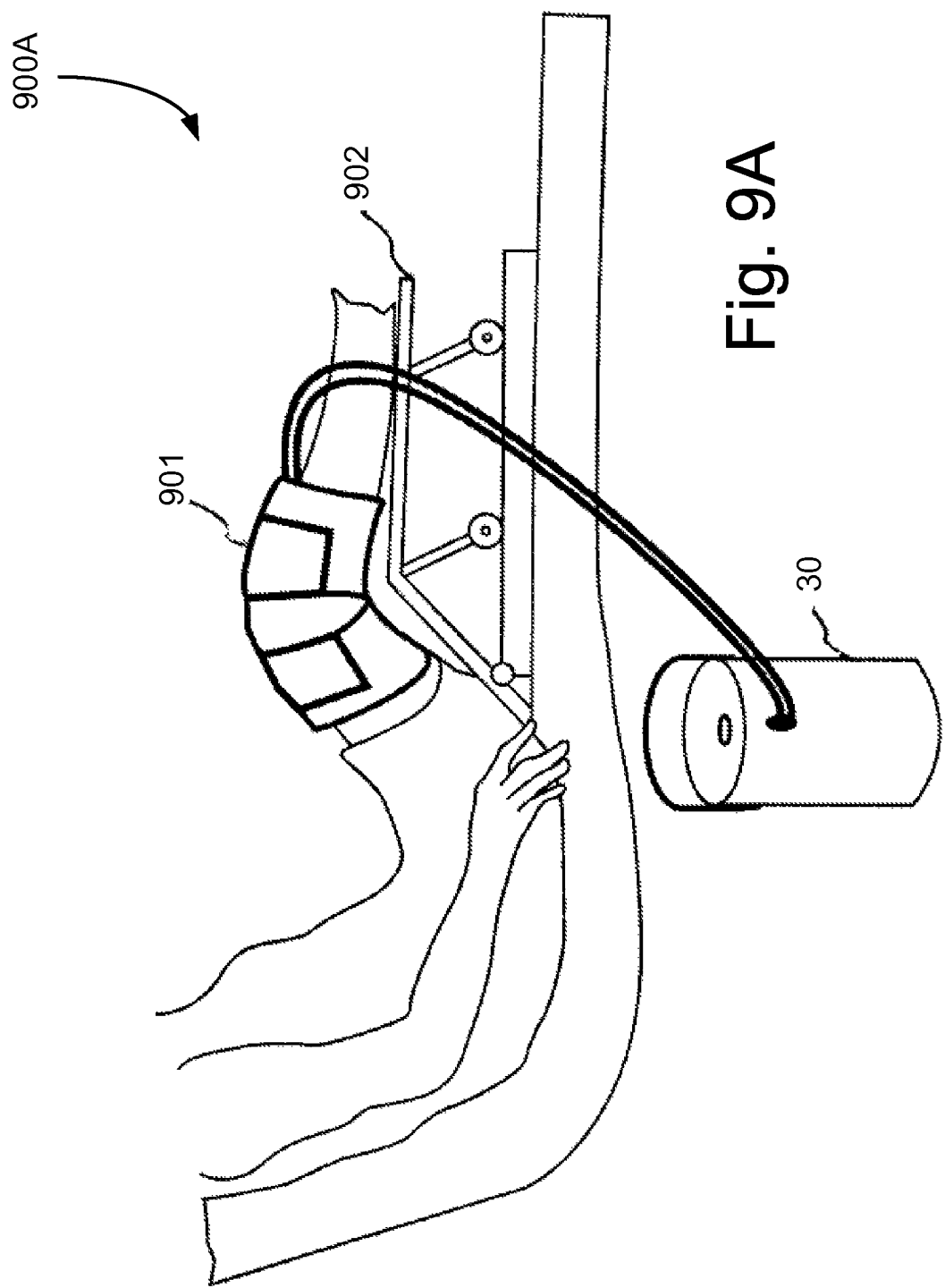
FIG. 9A is an illustration showing the application of contrast therapy in conjunction with continuous passive motion on a knee in flexure in accordance with an embodiment of the present invention.

FIG. 9A is an illustration showing the application of contrast therapy in conjunction with continuous passive motion on a knee in flexure in accordance with an embodiment of the present invention. In the pictured embodiment, a contrast therapy Thermal Exchange Layer 901 is shown applied to a therapy recipient's knee. A Portable Control Unit 30 supplies hot and/or cold fluid to the contrast therapy Thermal Exchange Layer 901. A Knee Brace and CPM Device Assembly 902 is shown, at 900A, with the knee in flexure. Alternatively, in some embodiment, the Therapeutic Knee Brace and CPM Device Assembly 902 may house the Contrast Therapy System 10 and supply hot and/or cold fluid to the contrast therapy Thermal Exchange Layer 901. As discussed in detail below, the instant invention provides hot, cold or contrast therapy to a therapy recipient throughout a therapeutic range of motion.

Figure 9B:
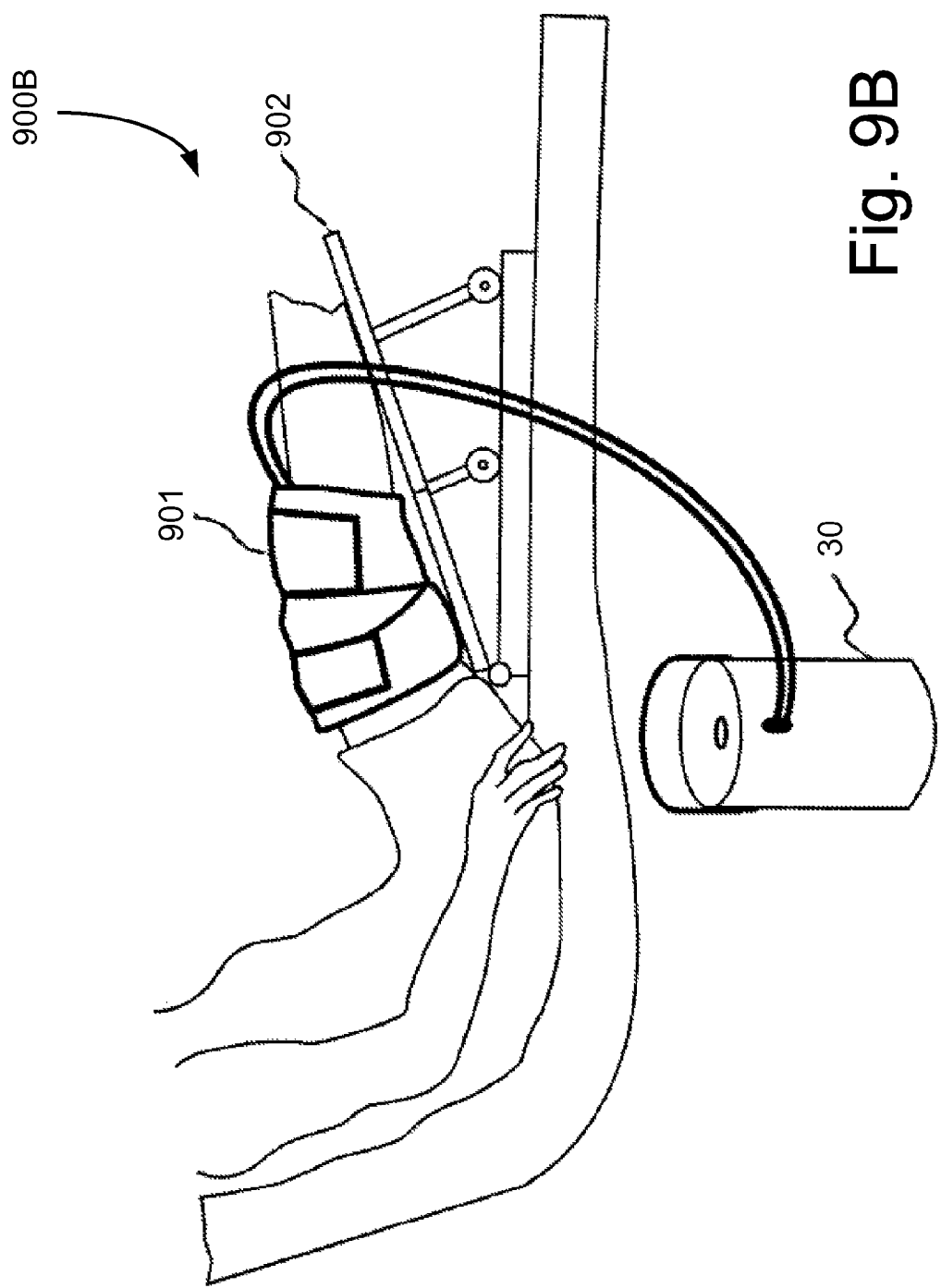
FIG. 9B is an illustration showing the application of contrast therapy in conjunction with continuous passive motion on a knee in extension in accordance with an embodiment of the present invention.

FIG. 9B is an illustration showing the application of contrast therapy in conjunction with continuous passive motion on a knee in extension in accordance with an embodiment of the present invention. FIGS. 9A and 9B depict the application of the instant device at either end of a range of therapeutic articulation. It should be understood that the instant invention provides compressive and thermal or contrast therapy throughout a therapeutic range of articulation. In the pictured embodiment, at 900B, a contrast therapy Thermal Exchange Layer 901 is shown applied to a therapy recipient's knee, with the knee in extension. A Portable Control Unit 30 supplies hot and/or cold fluid to the contrast therapy Thermal Exchange Layer 901. A Therapeutic Knee Brace and CPM Device Assembly 902 is shown having passively articulated the knee to a selected extension point.

FIGS. 9A and 9B also illustrate the use of the instant invention in conjunction with a Therapeutic Knee Brace and CPM Device Assembly 902. Thermal or contrast therapy may be provided throughout the range of motion of an implicated therapy site. As depicted, contrast therapy may be applied to a knee therapy site whether in flexure as shown in 900A, or in extension as shown in 900B. As discussed more fully below, the novel design of the active thermal exchange bladder of the instant invention allows full articulation through the entire therapeutic range of motion of any implicated therapy site.

Figure 10A:
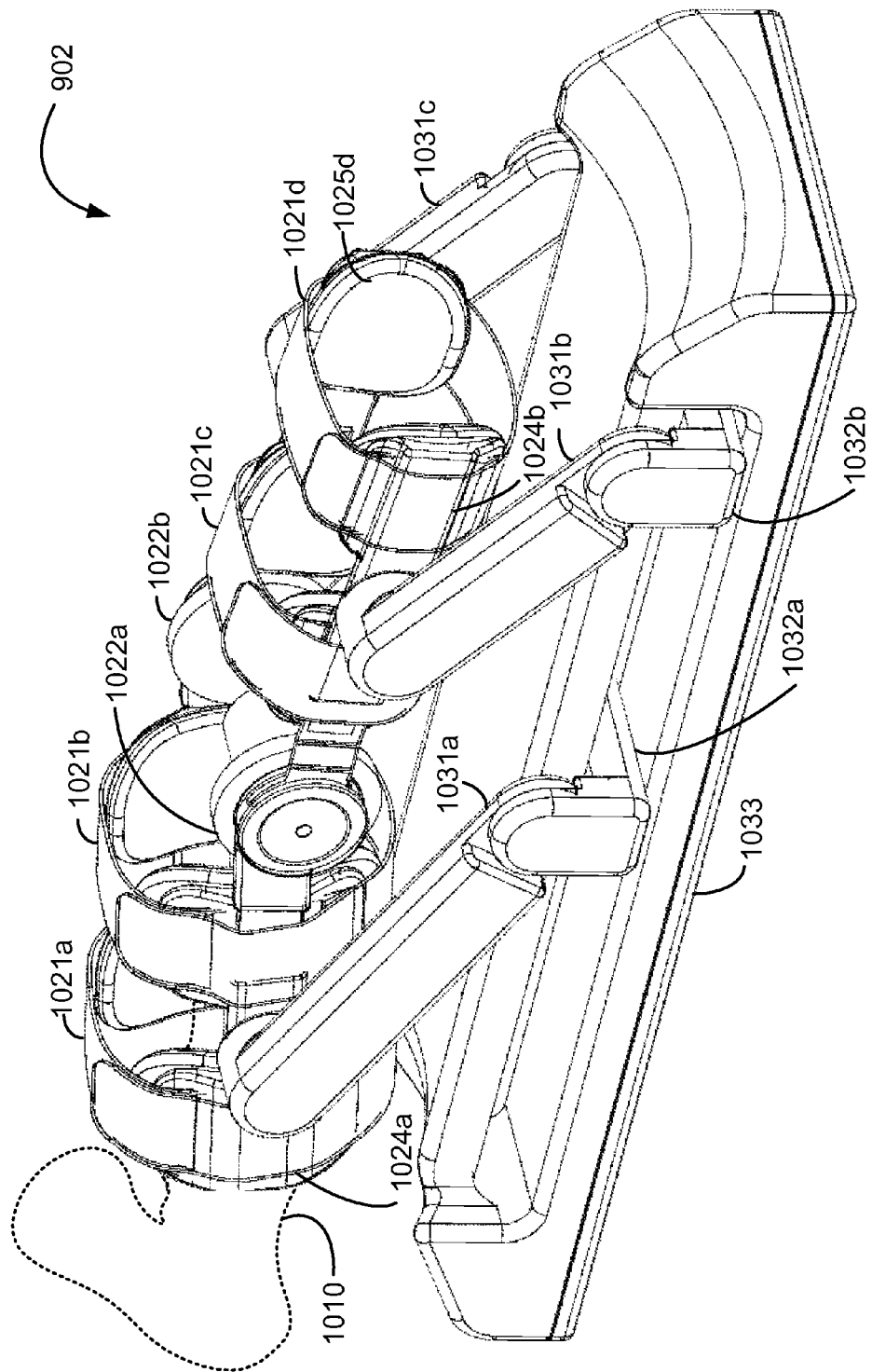
FIG. 10A is an isometric view of a therapeutic knee brace coupled with a continuous passive motion device in accordance with an embodiment of the present invention.
Figure 10B:
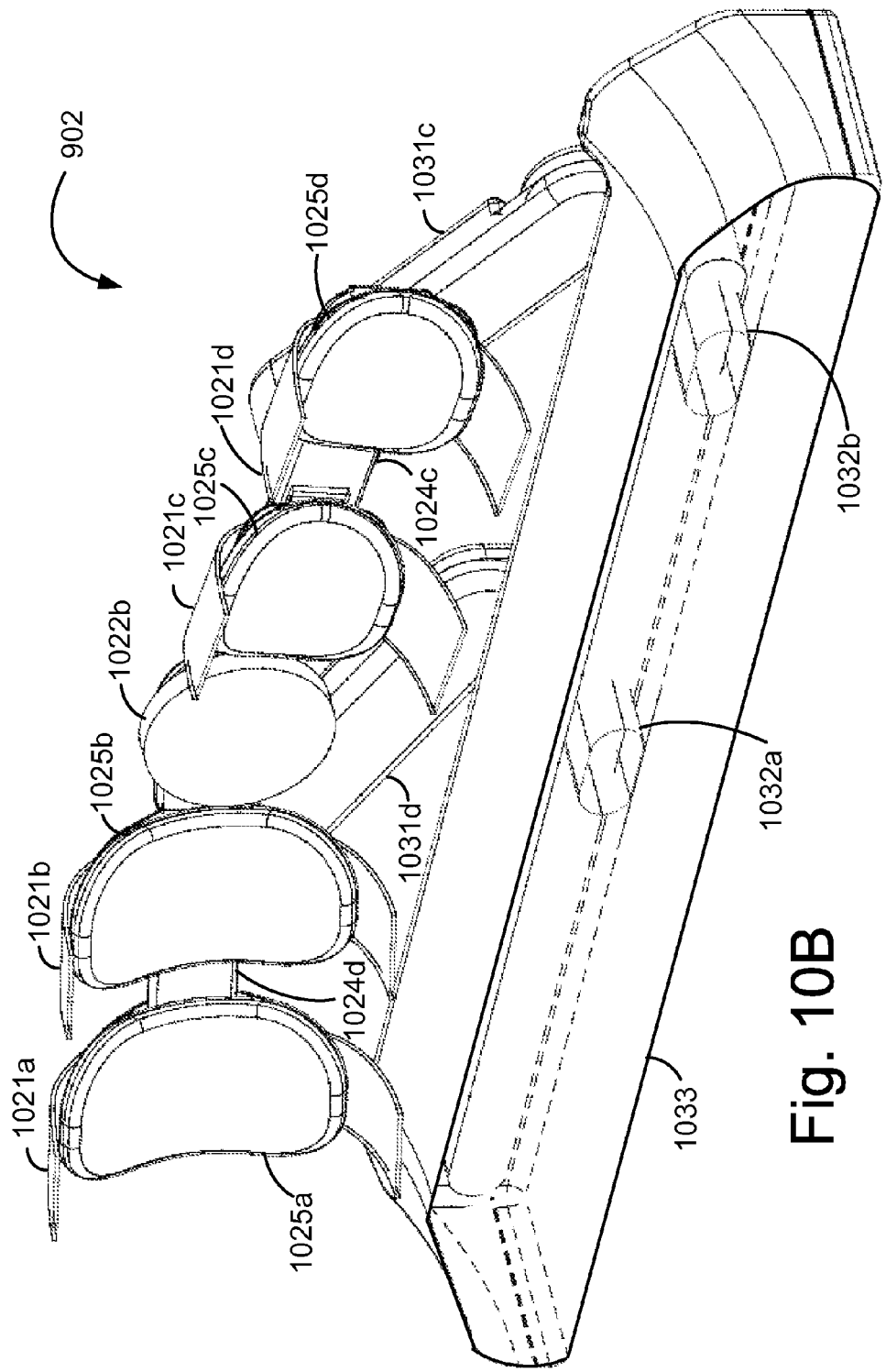
FIG. 10B is a cross-sectional view of a therapeutic knee brace coupled with a continuous passive motion device in accordance with an embodiment of the present invention.
Figure 10C:
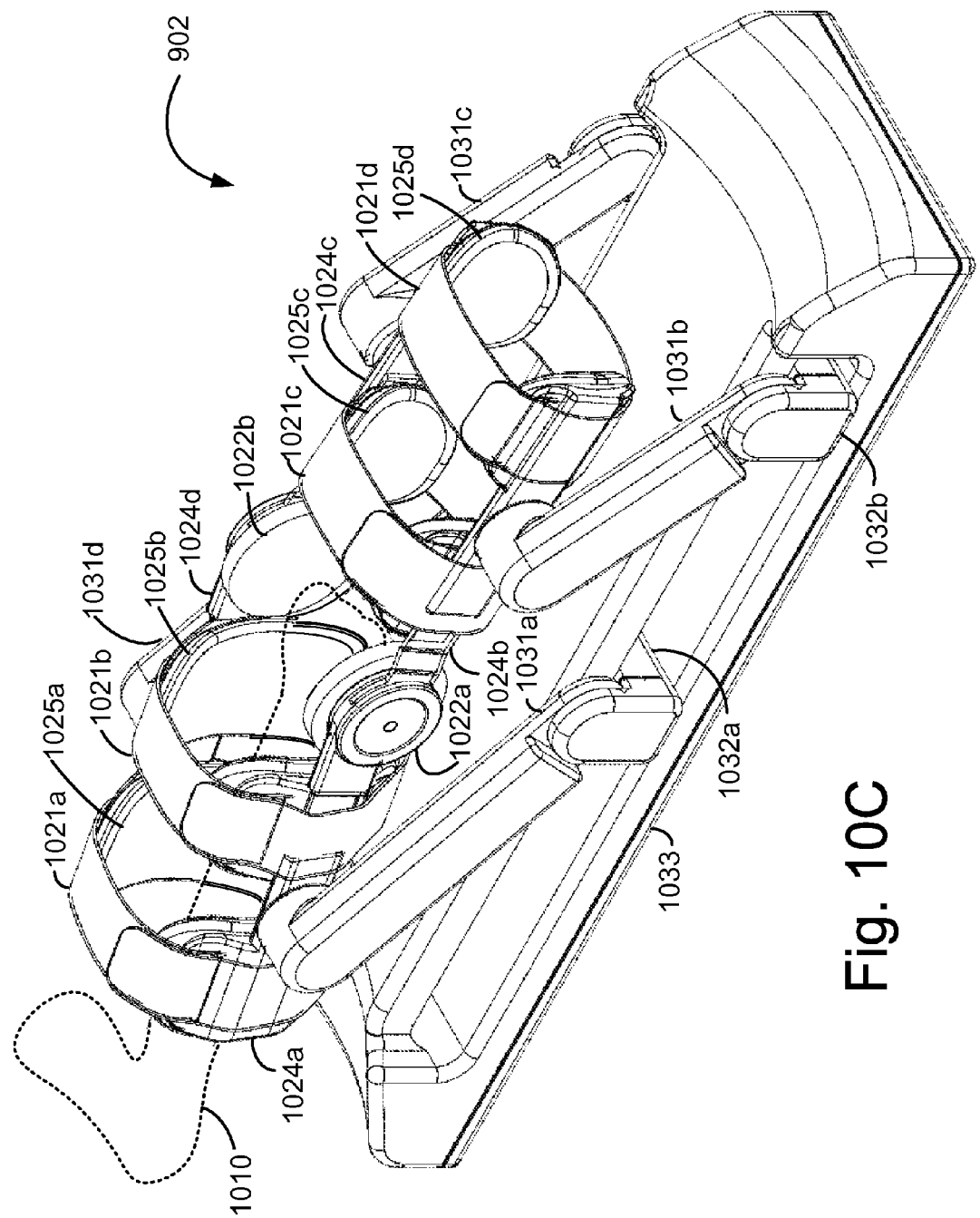
FIG. 10C is an isometric view of a therapeutic knee brace coupled with a continuous passive motion device in accordance with an embodiment of the present invention.

FIG. 10A is an isometric view of a therapeutic knee brace coupled with a continuous passive motion device in accordance with an embodiment of the present invention. Similarly, FIG. 10C is another isometric view of a therapeutic knee brace coupled with a continuous passive motion device in accordance with an embodiment of the present invention. In these Figures, the Knee Brace 1200 is shown coupled to the CPM Device 1300. FIG. 10B, on the other hand, is a cross-sectional view of a therapeutic Knee Brace 1200 coupled with a Continuous Passive Motion Device 1300 in accordance with an embodiment of the present invention.

The Knee Brace 1200 includes Leg Braces 1024 which provide support along the leg. In the present illustration four Leg Braces 1024a, 1024b, 1024c and 1024d are illustrated, however more or less supportive Leg Braces 1024 may be used to provide the desired level of support. Leg Braces 1024 are typically metal or composite thereby providing an adequate level of shock protection and stability; however additional materials may be utilized such as ceramics or polymers. In some embodiment the Leg Braces 1024 may be adjustable to extend or retract in length in order to provide a more versatile fit. Restraints 1021a, 1021b, 1021c and 1021d secure the Leg Braces 1024 to the therapy recipient's leg. In the present illustration the Restraints 1021 include four straps capable of circumventing the leg. Such straps may be adjustable elastic, and may be secured by hooks configured to releasably engage complimentary loops. Alternate Restraints 1021 may be utilized however. For example, Restraints 1021 may include rigid or semi-rigid arches that couple to the Leg Braces 1024. Alternatively, different numbers, widths or combinations of Restraints 1021 may be used.

The Leg Braces 1024 may couple with a Brace Joint 1022a, 1022b to provide flexion of the Knee Brace 1200 along the knee joint. In the present embodiment, a pair of rigid pivoting hinges are illustrated for the Brace Joint 1022a, 1022b. However, additional embodiments of the Brace Joint 1022 are acceptable. Such examples of alternate embodiments include a unilateral hinge, oblong hinge, or even a simple flexible site in the Knee Brace 1200. A flexion stop may be included into the Brace Joint 1022 to limit the angle of flexion and extension along the knee joint. Such a flexion stop is well known by those skilled in the art. Additionally, this allowable range of flexion may be configurable. This limitation on flexion allows for a physician to prescribe an acceptable range of extension and flexion, ensuring the knee joint is not overextended and thereby limiting possible damage to the knee joint. Additionally, the limits on flexion may encourage leg use by preventing a knee joint angle that incurs undue pain.

In some embodiment, the Brace Joint 1022 transmits the angle of flexion. Additionally, the configured allowable range of flexion of the knee brace may also be transmitted. These transmissions may be performed via mechanical, electrical, or wireless means. Transmission may be real time, thereby providing instantaneous, or near-instantaneous, information as to the angle of flexion of the Knee Brace 1200 and the configured range of flexion. Information as to the angle of flexion of the Knee Brace 1200 and range of flexion is of paramount importance when the Knee Brace 1200 is engaged with the CPM Device 1300 since the CPM Device 1300 actively flexes the Knee Brace 1200, and must do so within the allowable range of flexion.

In some embodiments, ergonomic Padding 1025a, 1025b, 1025c and 1025d may line the interior of the Knee Brace 1200. Padding 1025 may couple to the Leg braces 1024 to provide pinpoint cushioning along likely pressure points without hindering leg flexion. Alternatively, a Padding 1025 may be worn as a separate layer beneath the Leg Braces 1024. Padding 1025 may include separate pads as illustrated, or may be a single sheath. In some embodiment the Padding 1025 may be included in the Leg Brace 1024, or the Leg Braces 1024 may be sufficiently contoured, or of sufficiently flexible material, to warrant no Padding 1025.

A model of the Femur 1010 is illustrated to provide leg orientation within the Knee Brace 1200. The proximal end of the Femur 1010, including the hip, is seen protruding from the rear of the Knee Brace 1200. Correspondingly, the therapy recipient's thigh would occupy this region of the Knee Brace 1200. The knee joint is located between the hinges of the Brace Joint 1022. The calf region of the therapy recipient's leg extends through and beyond the lower portion of the Knee Brace 1200. In this way the therapy recipient's leg is elevated and the angle of flexion of the knee joint is highly controlled.

The CPM Device 1300 elevates and flexes the knee joint. CPM devices are well known by those skilled in the art; however, unlike traditional CPM devices, the illustrated CPM Device 1300 couples directly with the Knee brace 1200 via the actuator, illustrated as Pivoting Arms 1031*a*, 1031*b*, 1031*c* and 1031*d*. The Pivoting Arms 1031 are capable of pivoting at the Knee Brace 1200 juncture. In the present illustration, the Pivoting Arms 1031 couple to either Yoke 1032*a* or 1032*b* which provide support and may be capable of lateral movement along the Base 1033. The pivoting ability of the Pivoting Arms 1031 in conjunction with the lateral movement supplied by the Yokes 1032 allows for knee joint flexion and extension while maintaining a rotational axis along the hip joint that remains stationary while the hip joint rotates. By maintaining a stationary rotational axis along the hip joint, the therapy recipient's body may remain stationary during the CPM therapy, thereby increasing comfort and effectiveness. Additional configurations of Pivotal Arms 1031 and Yokes 1032 exist that provide a stationary rotational axis, and will be explored in more detail below.

Typically, a power source is housed within the Base 1033 which drives the moving of the Pivotal Arms 1031 and Yokes 1032. In some embodiment multiple power sources may be utilized to provide the manipulation. Power source(s) may be powered by direct or alternating current. Additionally, in some embodiment the power source may be external to the Base 1033. The power source may include a power source, hydraulics, third party force application, or any other force. The rate, duration and degree of movement of the Pivotal Arms 1031 and Yokes 1032 are configurable, either manually or automatically.

In some embodiment, the CPM Device 1300 includes a sensor capable of receiving transmission of information from the Knee Brace 1200 pertaining to the angle of flexion, as well as the configured allowable range of flexion. Such a sensor may receive information mechanically or electrically. In one embodiment, the sensor includes a receiver for receiving wireless signals from the Knee Brace 1200. Information from the sensor may be dynamically compiled such that the Pivotal Arms 1031 and Yokes 1032 movement never exceeds the configured range of flexion of the Knee Brace 1200. The communication of settings and physical conditions from the Knee Brace 1200 to the CPM Device 1300 dramatically enhances ease of use, while reducing potential operational errors.

FIG. 10B is a cross-sectional view of a therapeutic Knee Brace 1200 coupled with a Continuous Passive Motion Device 1300 in accordance with an embodiment of the present invention. The cross-sectional view more clearly illustrates the orientation of Padding 1025 in relation to the Leg Braces 1024.

The mechanism of the Yoke 1032 lateral movement is also clearer in the cross-sectional view. In one embodiment, the Base 1033 includes Channels 1334 that allow the Yoke 1032 to engage and slide along the Base's 1033 long axis, thereby enabling lateral movement of Yokes 1032.

Figure 10D:
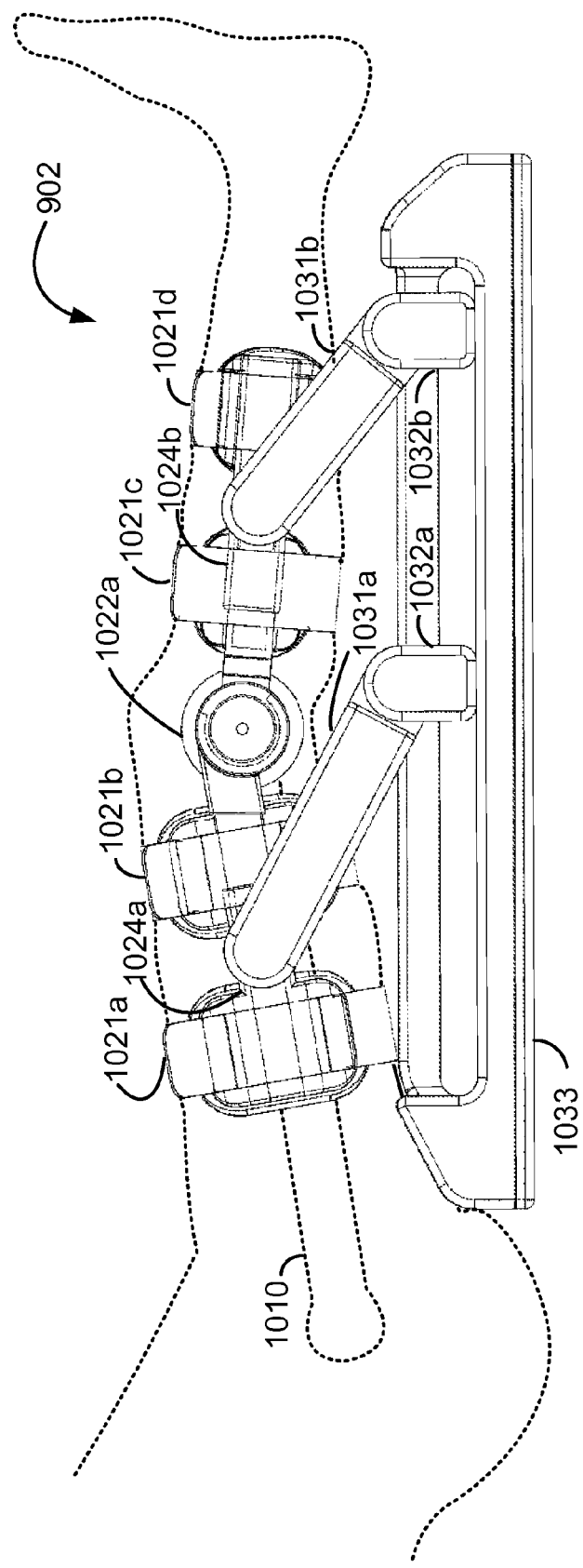
FIG. 10D is a side view of a therapeutic knee brace coupled with a continuous passive motion device illustrating wearer orientation in accordance with an embodiment of the present invention.

FIG. 10D is a side view of a therapeutic Knee Brace 1200 coupled with a Continuous Passive Motion Device 1300 illustrating wearer orientation in accordance with an embodiment of the present invention. In this Figure the therapy recipient is shown engaged in the Knee Brace 1200 to further clarify the orientation of the Knee Brace 1200 when worn. Furthermore, the Femur 1010 is shown to provide additional orientation. The Restraints 1021 engage the therapy recipient's leg securely. The base of the leg and hip rest against the anterior of the CPM device Base 1033. The Hip Joint, as seen at the end of the Femur 1010, remains stationary, within the viewing plane, as the Knee Brace 1200, and subsequently the therapy recipient's leg, are flexed by the CPM Device 1300. Hip joint will rotate when undergoing CPM therapy. Therapy recipient may recline or semi-recline while undergoing CPM therapy. The present illustration shows no support for the therapy recipient's foot, however additional embodiments may include foot cradles, both stationary and CPM enabled.

Figure 10E:
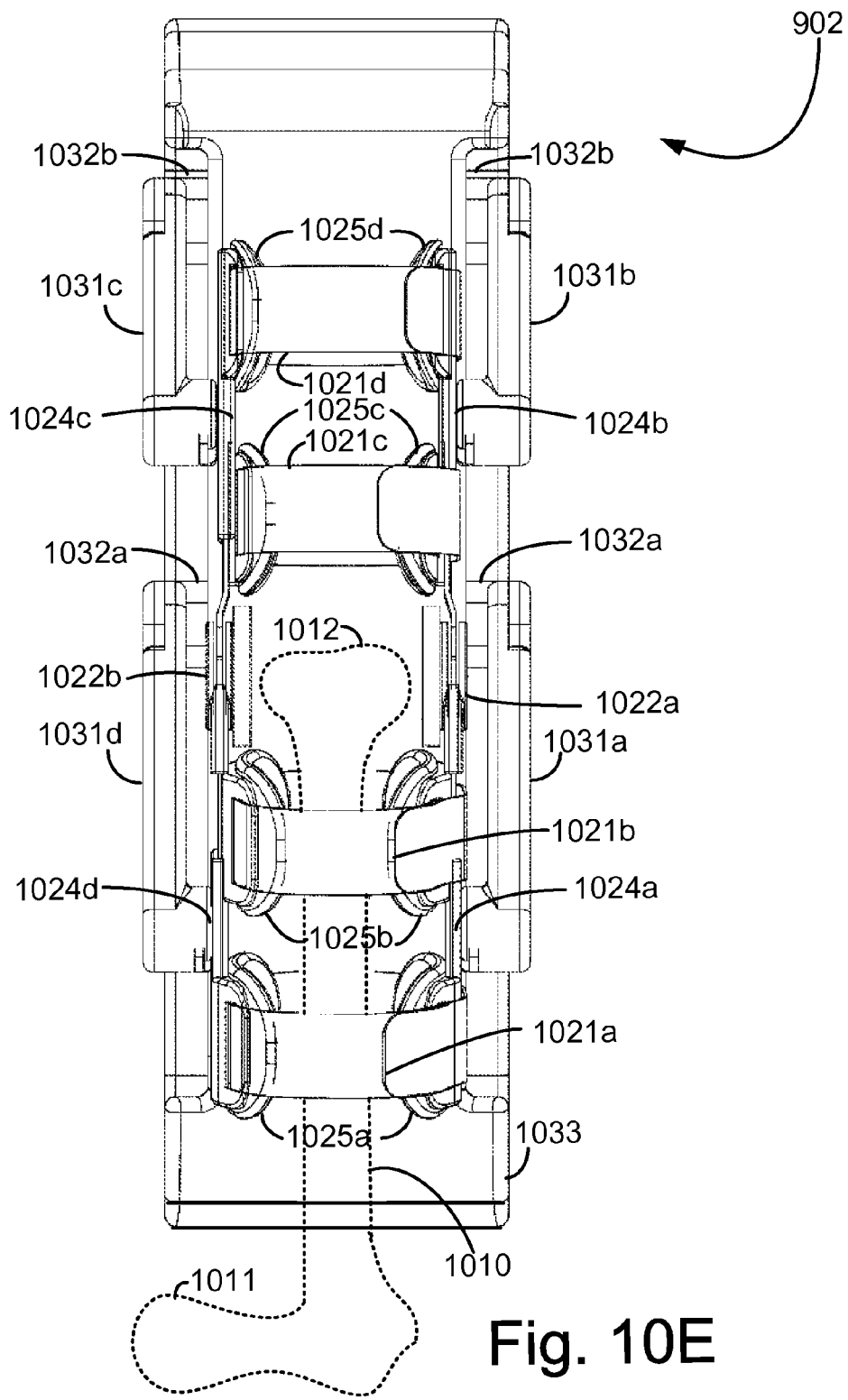
FIG. 10E is a top view of a therapeutic knee brace coupled with a continuous passive motion device in accordance with an embodiment of the present invention.

FIG. 10E is a top view of a therapeutic Knee Brace 1200 coupled with a Continuous Passive Motion Device 1300 in accordance with an embodiment of the present invention. This illustration shows the symmetrical nature of the Knee Brace 1200 coupled with the CPM Device 1300. Such symmetry is not required, and in another embodiment the Knee Brace 1200 and/or the CPM Device 1300 may have significant asymmetry as long as functional requirements are met.

Additionally, the Femur 1010 is clearly shown. The Hip Joint 1011 is seen protruded from the Knee Brace 1200. The Knee Joint 1012 is seen located adjacent the Brace Joint 1022.

Figure 11:
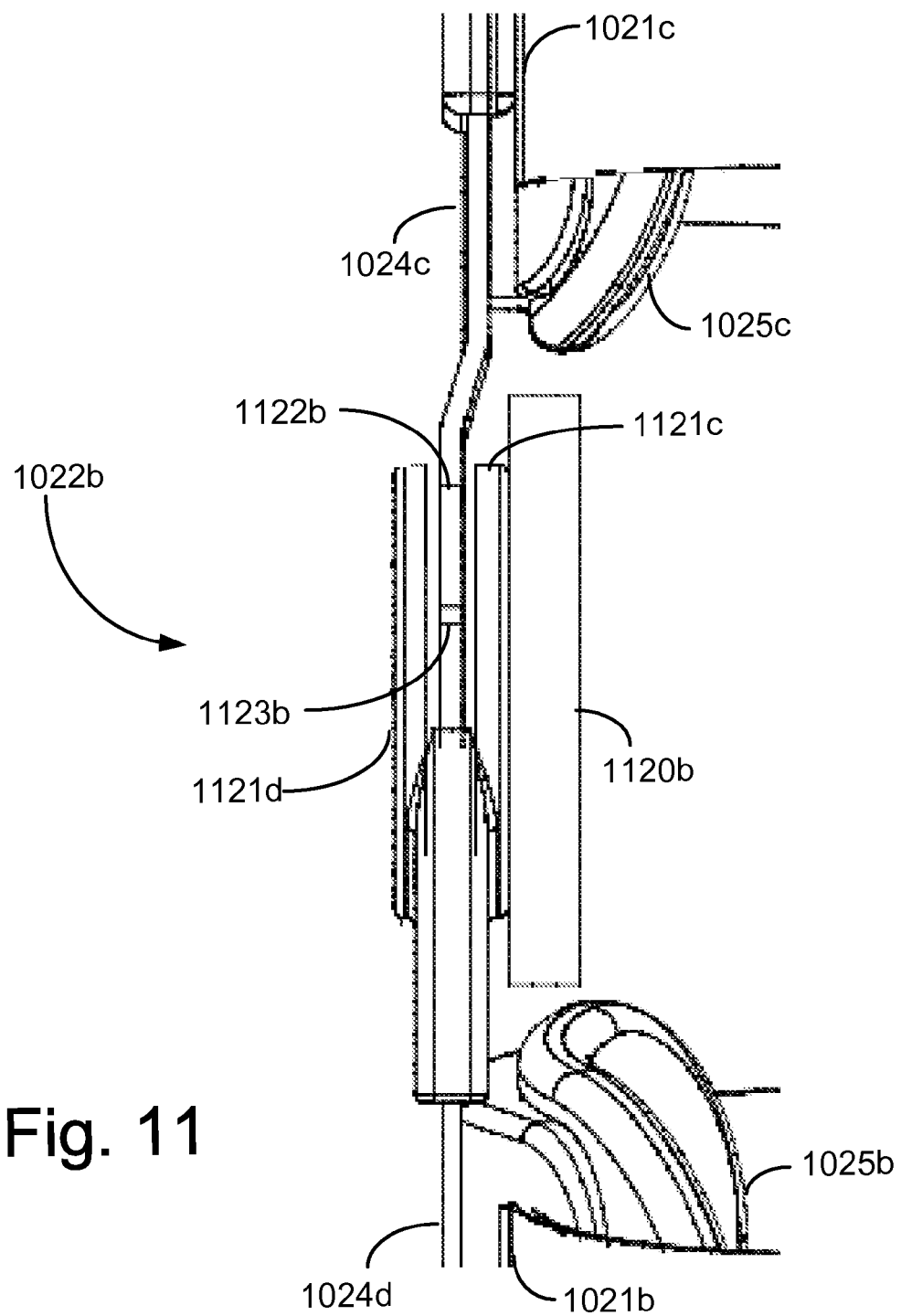
FIG. 11 is a top view of a knee brace joint in accordance with an embodiment of the present invention.

FIG. 11 is a top view of a knee Brace Joint 1022*b* in accordance with an embodiment of the present invention. The Brace Joint 1022*b* includes a circular Interior Washer 1122*b* coupled to the first Leg Brace 1024*c*. Circular Exterior Washer 1121*c* and circular Exterior Washer 1121*d* flank the Interior Washer 1122*b*. Exterior Washers 1121 are coupled to the second Leg Brace 1024*d*. Exterior Washers 1121 and Interior Washer 1122*b* include a circular perforation at the center of each washer. A Pin 1123*b* couples the Exterior Washers 1121 to the Interior Washer 1122*b* by engaging at the perforation. Pin 1123*b* allows for independent rotation of the Interior Washer 1122 in relation to the Exterior Washers 1121, thereby creating a hinge between the first and second Leg Braces 1024.

In some embodiment, it is desirable that there is a low coefficient of friction between the surfaces of the Exterior Washers 1121 and the Interior Washer 1122*b* to promote fluid rotation of the hinge. A lubricant may be applied to provide such fluid motion. Alternatively, the materials chosen to construct the Exterior Washers 1121 and Interior Washer 1122*b* may be catered to provide a low coefficient of friction. In some embodiment, a higher coefficient of friction may be desired between the surfaces of the Exterior Washers 1121 and the Interior Washer 1122*b* to provide a stiffer Brace Joint 1022 and therefore more stability of the knee joint. Additionally, a Padded Layer 1120*b* may be included between the therapy recipient and the rest of the Brace Joint 1022*b*.

Additionally, the Brace Joint 1022 may include a flexion stop capable of limiting the range of Brace Joint 1022 flexion and extension. Such a flexion stop may be configurable by the therapy recipient, physician, or personal caregiver to provide a range of flexion most conducive to proper healing and limiting pain. Overextension of the knee joint may lead to additional joint and ligament damage; therefore the flexion stop may prevent such damage.

Additionally, in some embodiment the Brace Joint 1022 may be capable of dynamic transmission of the range of flexion, as defined by the flexion stop, as well as the instant angle of flexion. As earlier stated, these transmissions may be performed via mechanical, electrical, or wireless means. Transmission may be real time, thereby providing instantaneous information as to the angle of flexion of the Knee Brace 1200 and the configured range of flexion. Information as to the angle of flexion of the Knee Brace 1200 and range of flexion is of paramount importance when the Knee Brace 1200 is engaged with the CPM Device 1300 since the CPM Device 1300 actively flexes the Knee Brace 1200, and must do so within the allowable range of flexion.

It is important to note that a variety of Brace Joint 1022 configurations may be utilized as is well known by those skilled in the art. For instance Brace Joint 1022 may provide additional planes of movement, or may be elongated as to contour to the knee joint.

Figure 12A:
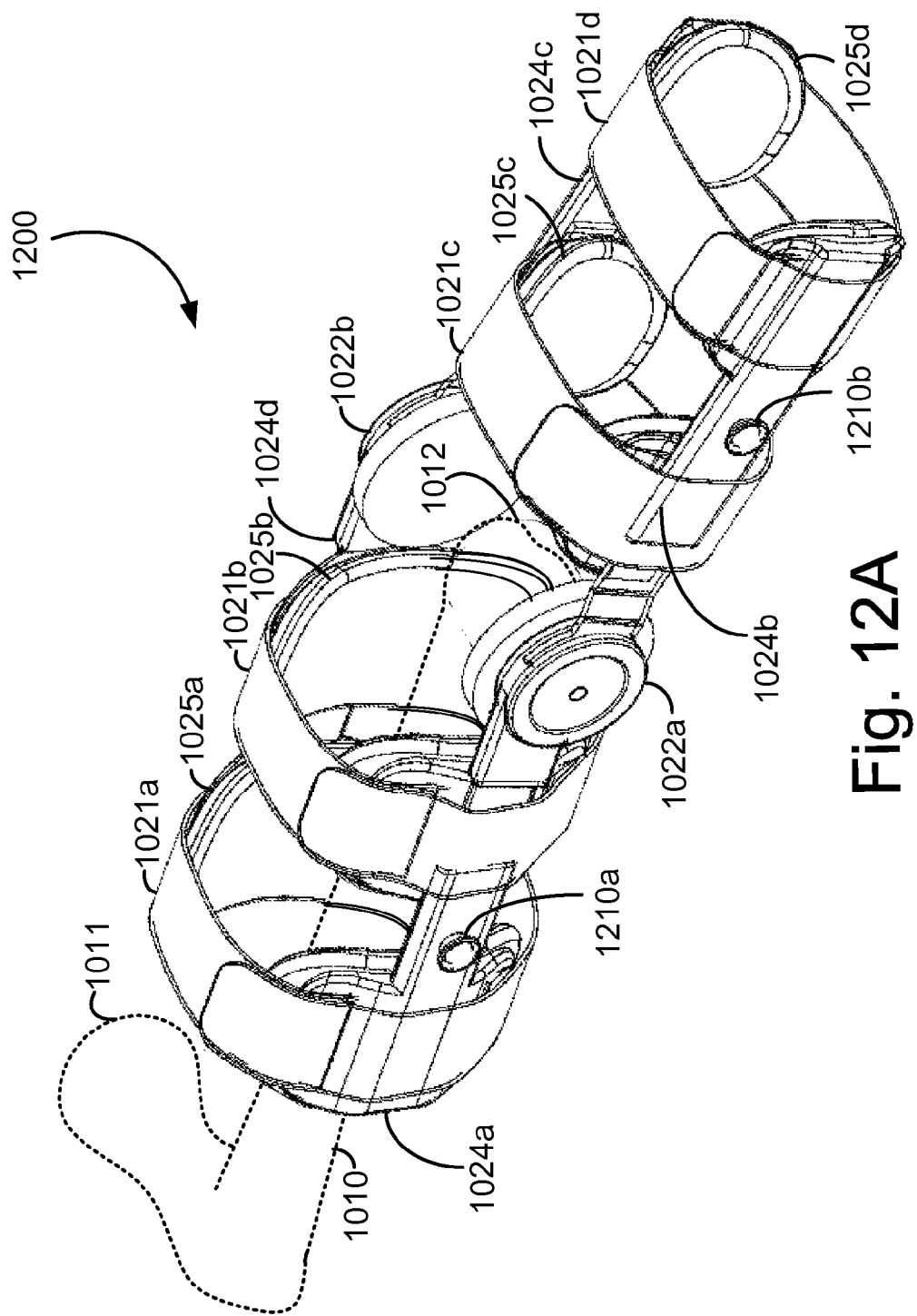
FIG. 12A is an isometric view of a therapeutic knee brace in accordance with an embodiment of the present invention.
Figure 12B:
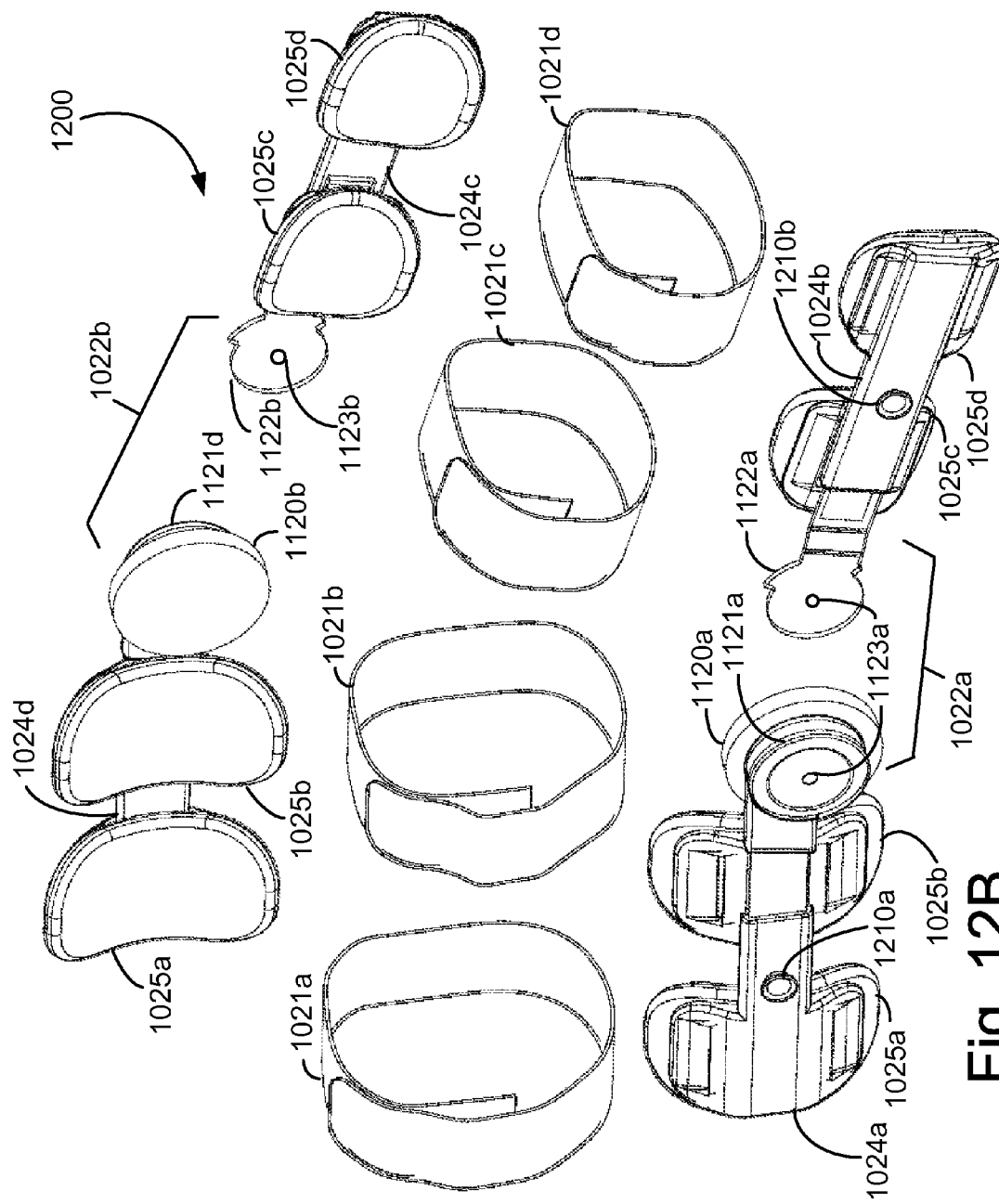
FIG. 12B is an exploded view of a therapeutic knee brace in accordance with an embodiment of the present invention.
Figure 12C:
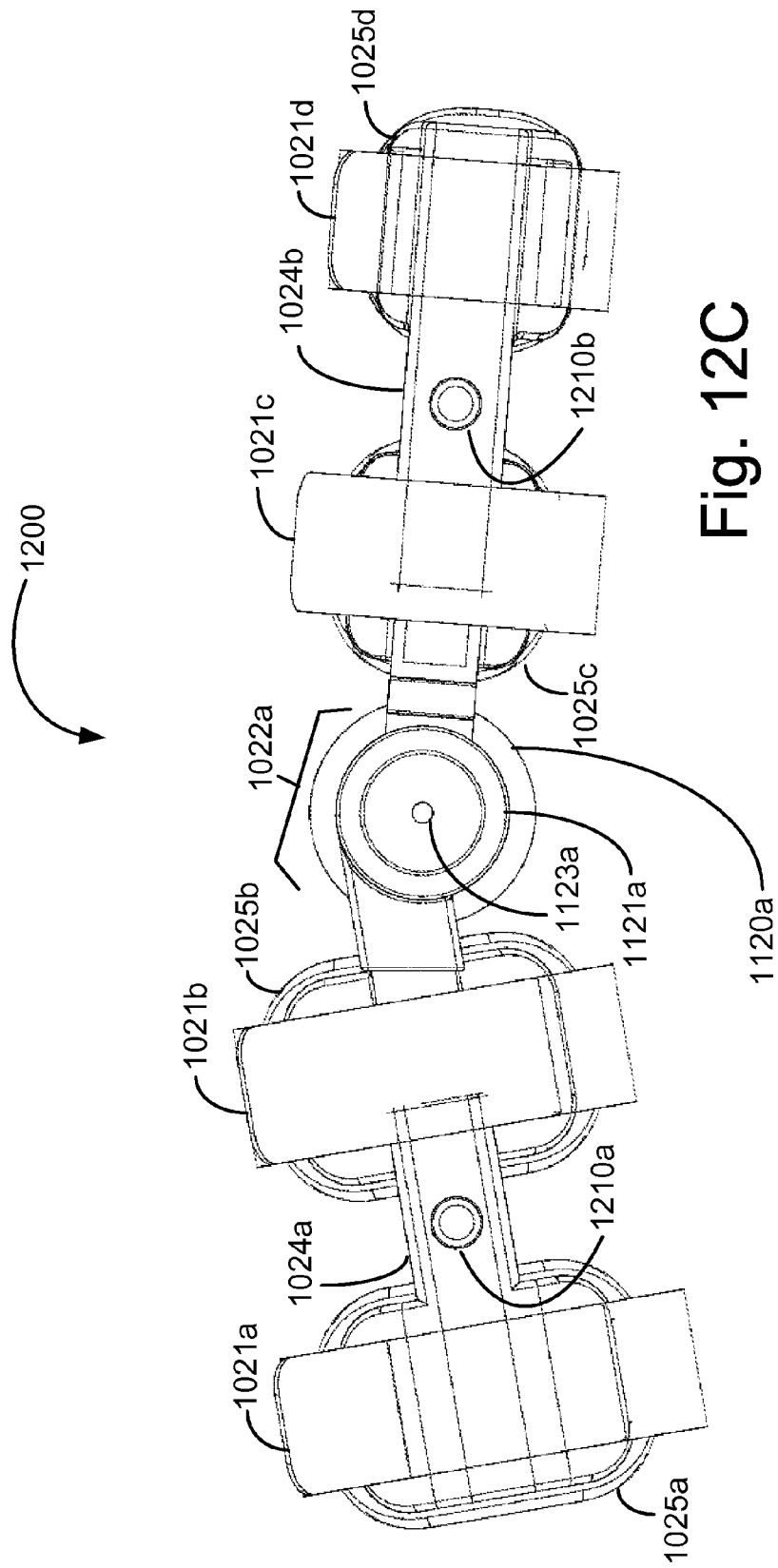
FIG. 12C is a side view of a therapeutic knee brace in accordance with an embodiment of the present invention.

FIG. 12A is an isometric view of a therapeutic Knee Brace 1200 in accordance with an embodiment of the present invention. FIG. 12B is an exploded view of a therapeutic Knee Brace 1200 in accordance with an embodiment of the present invention. Additionally, FIG. 12C is a side view of a therapeutic Knee Brace 1200 in accordance with an embodiment of the present invention.

These illustrations clearly show the Knee Brace 1200 separate from the CPM Device 1300. Most importantly the coupling site on the Leg Braces 1024 is visible in these illustrations. Each coupling site includes a Peg 1210*a*, 1210*b* designed to engage with a complementary Grove 1335 located upon the Pivoting Arm 1031 of the CPM Device 1300. Pegs 1210 are designed to easily drop into the Groves 1335 without much effort, thereby providing extreme ease of CPM therapy. However, despite the ease of engaging the Pegs 1210 into the complementary Groves 1335, the design provides for a secure mount for the Knee Brace 1200 on the CPM Device 1300. Additionally, the Pegs 1210 allow for selective coupling and decoupling of the Knee Brace 1200 to the CPM Device 1300. For instance, Peg 1210 size and configuration may allow only certain models of the Knee Brace 1200 to engage other specific models of the CPM Device 1300. Of course, additional alternate systems of selective coupling of the Knee Brace 1200 to the CPM Device 1300 may be utilized as is known by those skilled in the art.

FIG. 12B is an exploded view of a therapeutic Knee Brace 1200 in accordance with an embodiment of the present invention. This view provides for a clear conceptualization for one embodiment of the Knee Brace 1200.

As shown there are four Restraints 1021 that consist of straps that are capable of adjustably circumventing the wearer's leg. Each Restraint 1021 loops through two Leg Braces 1024 which are located on opposing sides of the therapy recipient's leg. Restraints 1021, as shown, are capable of adjustment by and may be made from elastic material. The amount of elasticity a particular Restraint 1021 has may be selected according to a desired application, or range of applications. In some embodiments, the Restraints 1021 are designed to stretch to approximately 150%-200% of their unstretched length, however less elastic and more elastic Restraints 1021 may be used. The Restraints 1021 may be variously sized, and are usually at least as long as required to wrap around the therapy recipient's leg in order to secure the Knee Brace 1200 to the therapy site. Restraints 1021 usually include a surface of loops that are adapted to detachably receive complementary hooks. The hooks and loops are positioned so that the hooks may engage the loops when the Restraints 1021 are wrapped around the wearer's leg. The Restraints 1021 may be adjusted to desired tensions and may be fixed by engaging the hooks and the loops together. The hooks and loops may subsequently be disengaged, so that the tension may be adjusted, for instance, and reengaged at will. In some embodiments, a wrap lock, or other appropriate system, may alternatively be used to secure the Knee Brace 1200 to the therapy recipient's leg.

The Leg Braces 1024 provide the structural support for the Knee Brace 1024 and include coupling sites for the Restraints 1021, Padding 1025 for increased comfort, and Pegs 1210 for coupling to the CPM Device 1300. Leg Braces 1024 couple directly to the hinge of the Brace Joint 1022. Additionally, Leg Braces 1024 may be designed to have adjustable lengths. Of course, additional alternate designs for the Leg Brace 1024 may be utilized as is well known by those skilled in the art.

The Brace Joint 1022 provides for flexion of the Knee Brace 1200 along the knee joint. Details of the Brace Joint 1022 are addressed above.

Figure 13A:
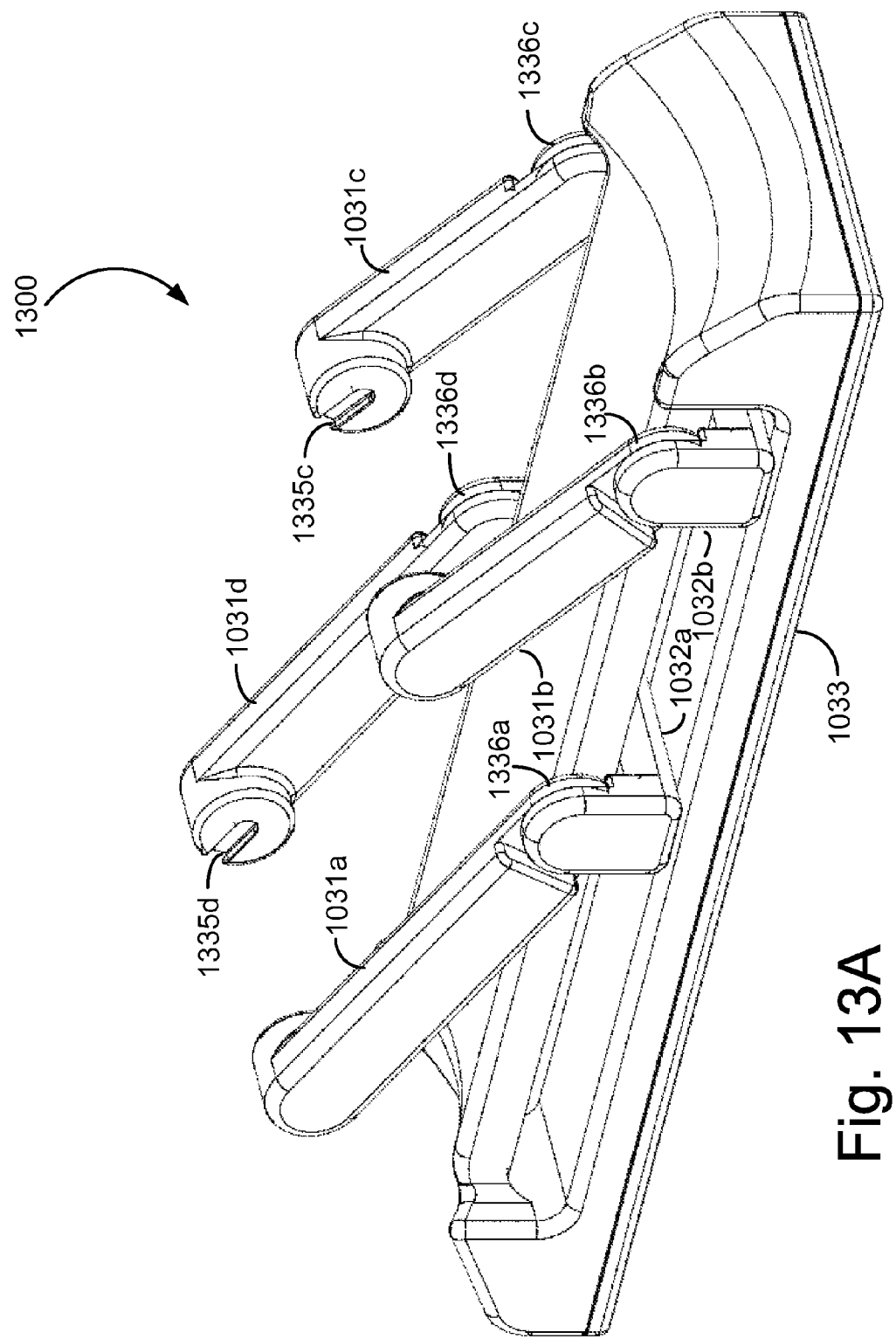
FIG. 13A is an isometric view of a continuous passive motion device in accordance with an embodiment of the present invention.

FIG. 13A is an isometric view of a Continuous Passive Motion Device 1300 in accordance with an embodiment of the present invention. Additionally, FIG. 13B is a side view of a Continuous Passive Motion Device 1300 in accordance with an embodiment of the present invention. These views provide for a clear conceptualization for one embodiment of the CPM Device 1300.

The illustrated CPM Device 1300 is designed to selectively engage with the therapeutic Knee Brace 1200. Groves 1335 located on the Pivoting Arms 1031 are designed to receive complimentary Pegs 1210. The Pivoting Arms 1031 are capable of pivoting at the peg-grove coupling site. Additionally, the Pivoting Arms 1031 are capable of pivoting at the Junction 1334 with the Yoke 1032. Each Yoke 1032 provides support for the Pivoting Arms 1031. Additionally, each Yoke 1032 is capable of lateral movement along the long axis of the Base 1033. Channels 1334 exist on either side of the Base 1033. The Yokes 1032 engage the Channels 1334, and the Channels 1334 provide a track for the lateral movement for the Yokes 1032.

The Base 1033 provides support for the CPM Device 1300. Additionally, in some embodiments the power source required to move the Pivoting Arms 1031 and Yokes 1032 may be housed within the Base 1033. In some embodiments, the Contrast Therapy System 10 may also be housed within the Base 1033. Alternatively, a Portable Unit 30 may be utilized when more mobility of thermal therapy is desired.

Additional alternate embodiments of the CPM Device 1300 exist, as is well known by those skilled in the art. For instance more Pivoting Arms 1031 may be included, or a foot cradle could be utilized.

Figure 14A:
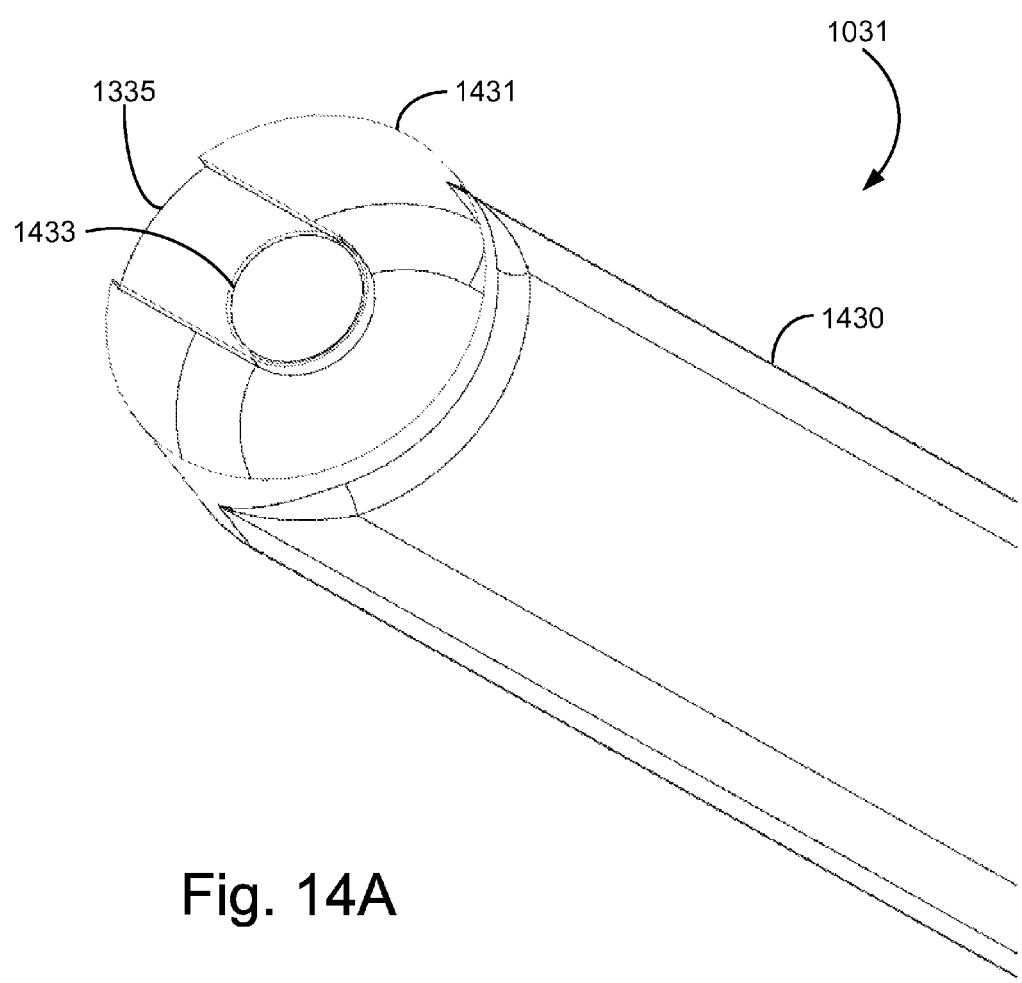
FIG. 14A is a cross-sectional view of a pivoting arm of a continuous passive motion device in accordance with an embodiment of the present invention.

FIG. 14A is a cross-sectional view of the Pivoting Arm 1031 of the Continuous Passive Motion Device 1300 in accordance with an embodiment of the present invention. This view more clearly illustrates the Grove 1335 capable of coupling with the Peg 1210 located on the Knee Brace 1200. The Grove is located on the Cap 1431 of the Pivoting Arm 1031. The Cap 1431 is coupled to the Shaft 1430 of the Pivoting Arm 1031. The Grove 1335 ends in a termination site. The termination site may be larger than the grove to allow the Peg 1210 a secure fit when engaging the Pivoting Arm 1031. In the Present illustration the Head 1433 of the Peg 1210 is seen engaged in the termination site of the Grove 1335.

Figure 14B:
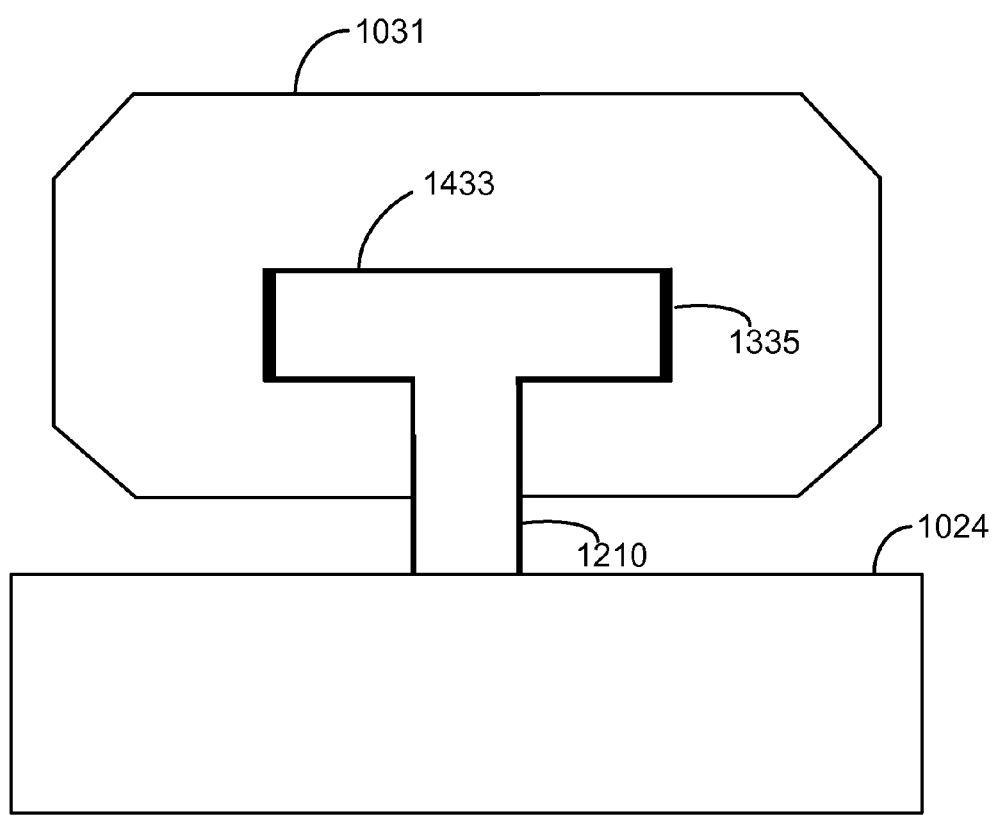
FIG. 14B is a cross-sectional view of a pivoting arm coupled with a leg brace in accordance with an embodiment of the present invention.

FIG. 14B is a cross-sectional view of a Pivoting Arm 1031 coupled with a Leg Brace 1024 in accordance with an embodiment of the present invention. In this view the Peg 1210 is seen extending up from the Leg Brace 1024. The Head 1433 of the Peg 1210 is larger than the peg shaft. The Grove 1335 of the Pivoting Arm 1031 encircles the peg Head 1433 in such a way as to ensure a secure coupling of the Pivoting Arm 1031 to the Leg Brace 1024.

Active Thermal Exchange Bladder

The novel design of the bladder of the instant invention allows for active or passive articulation of a therapy site while providing continuous thermal therapy and constant compression. The pad may be used in conjunction with the CPM Device 1300 to provide continuous thermal therapy and constant compression throughout a therapeutic range of flexion.

Figure 15A:
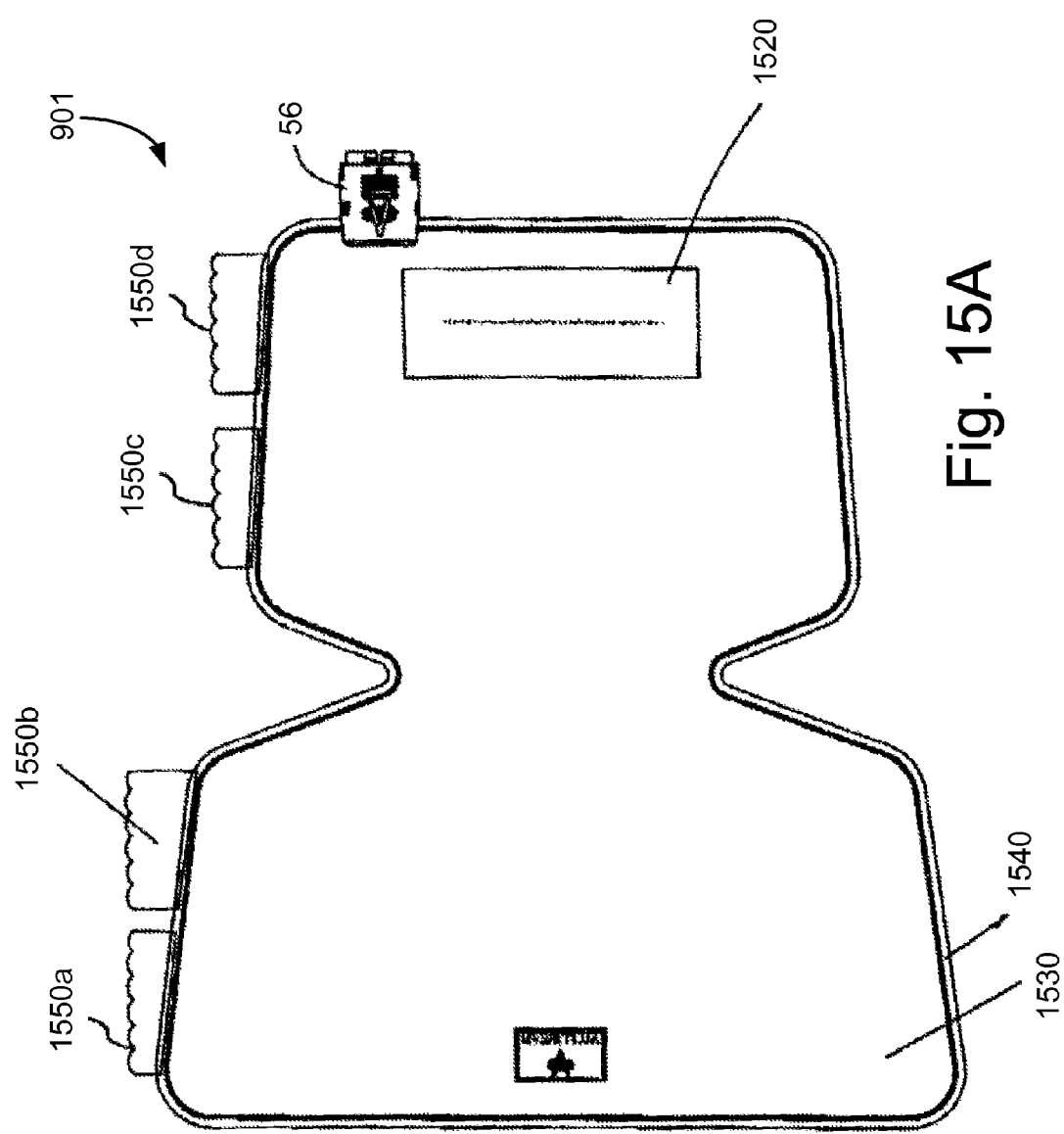
FIG. 15A is a top plan view of a first face of a knee thermal exchange layer adapted for use with a continuous passive motion device in accordance with an embodiment of the present invention.
Figure 15B:
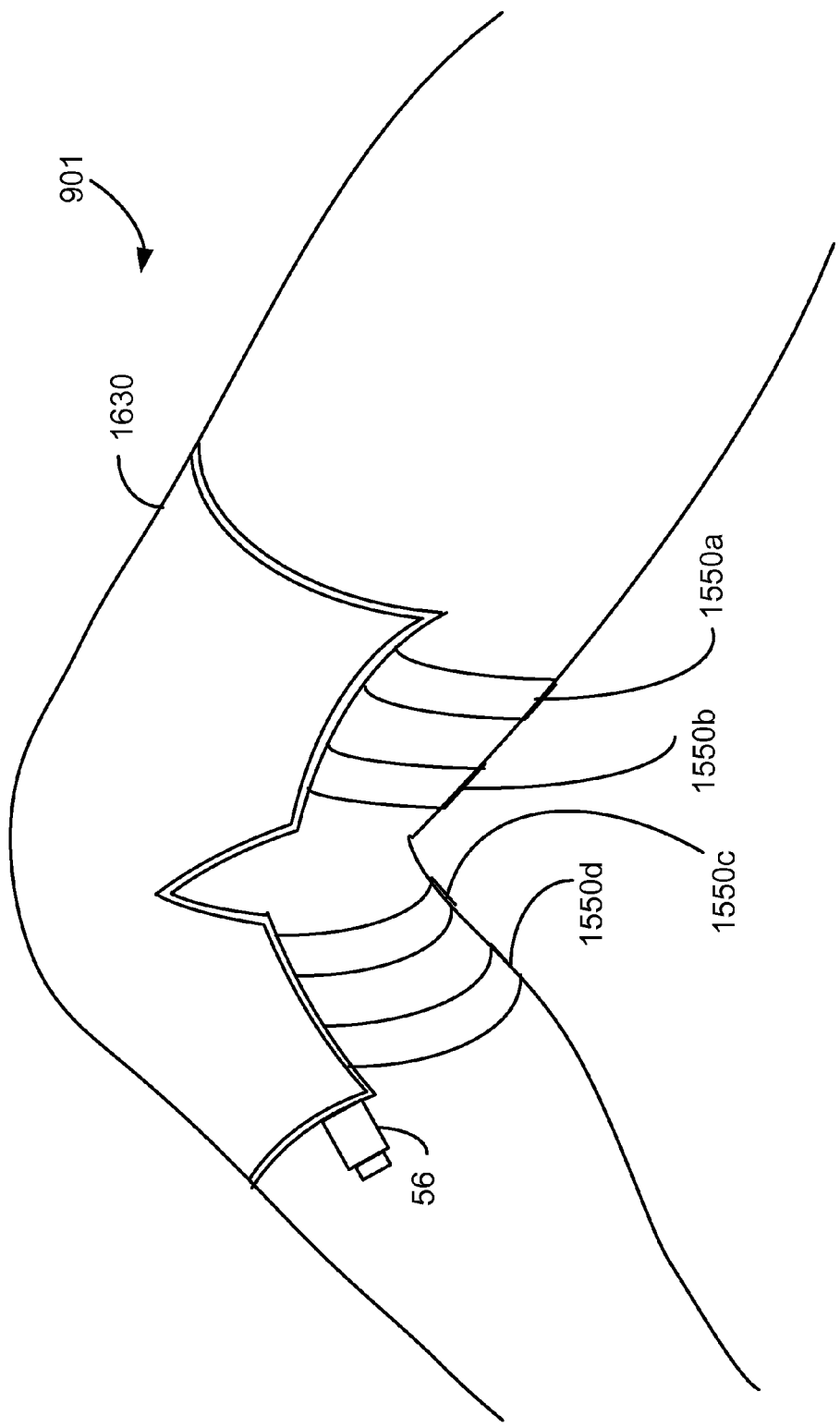
FIG. 15B is an isometric view of a knee thermal exchange layer wrapped around a therapy recipient in accordance with an embodiment of the present invention.

FIG. 15A is a top plan view of a Second Face 1530 of a knee Thermal Exchange Layer 901 adapted for use with a continuous passive motion device in accordance with an embodiment of the present invention. FIG. 15B is an isometric view of a knee therapy pad wrapped around a therapy recipient in accordance with an embodiment of the present invention. The Thermal Exchange Layer 901 includes a bladder envelope for holding an active thermal exchange Bladder 1700, as shown in FIGS. 16 and 17. The bladder envelope may be configured to impart a particular shape to the Bladder 1700, and/or the envelope may be configured to flex, stretch, bend, deform, and/or otherwise change shape, thus allowing the pad to more closely correspond to the precise shape of a therapy site. The Bladder 1700 and/or envelope may be configured to allow a limited amount of shape change, or conversely, unrestricted shape change.

In the pictured embodiment, a First Face of the stretchable bladder envelope is indicated generally in FIG. 16 at 1630. An opposing Second Face of the bladder envelope is indicated in FIG. 15A at 1530. The opposing faces converge at a perimeter 1540 of the bladder envelope, and collectively define a volume adapted to receive a thermal exchange Bladder 1700 which is shown in FIG. 17. The faces may be permanently sealed together at the Perimeter 1540. For example, the faces may be stitched, glued, stapled, etc. In some embodiments, the faces may be selectively sealed, such as by zipper, snaps, buttons or other releasable sealing mechanism. In some embodiments, portions of the Perimeter 1540 may be permanently sealed, while other portions are selectively sealed. Furthermore, some portions of the Perimeter 1540 may be left unsealed. In particular, an unsealed opening may be left to allow a thermal exchange Bladder 1700 to couple with a control unit, such as via a Fluidic Coupling Assembly 56, so that therapy fluid may be supplied to the thermal exchange Bladder 1700, thus permitting the Bladder 1700 to function as an active thermal exchange Bladder 1700.

In some embodiment, the First Face 1630 may be constructed of a material suitable to releasably engage the Second Face 1530. For instance, the First Face 1630 may be constructed of a mesh material and the Second Face 1530 may be constructed of a stretchable loop material configured to releasably receive complementary hook material, although other materials may be used. In some embodiments, the Second Face 1530 may be at least partially elastic; and in some embodiments, the Second Face 1530 may include structural supports to help establish a desire predefined shape for the Thermal Exchange Layer 901. First Face 1630 is generally constructed from a material suitable for placement next to the skin and adapted to facilitate heat transfer. For example, First Face 1630 may be constructed from cotton, nylon, polyester, or other fabrics. The First Face 1630 may have a mesh or other openwork design, as well as uninterrupted designs. In some embodiments, the First Face 1630 may be at least partially elastic; and in some embodiments, the First Face 1630 may include structural supports to help establish a desired predefined shape for the Thermal Exchange Layer 901. Because at least one of the First Face 1630 and the Second Face 1530 may be constructed from a flexible material, volume may be deformable, meaning that the size and shape of the volume may change as the First Face 1630 and/or Second Face 1530 flexes, stretches, bends, deforms, and/or otherwise changes shape. In general, the volume may be dimensioned to closely accommodate a particular thermal exchange Bladder 1700, without leaving an abundance of unoccupied space when the Bladder 1700 is positioned in the volume, although additional space may be present. Either said face may also include an informational tab 1520 displaying instructions on the proper application and use of the Thermal Exchange Layer 901. The above described configuration is provided as an illustrative example, and other arrangements may be used for holding the thermal exchange Bladder 1700.

The knee Thermal Exchange Layer 901 includes an adjustable strapping system 1550. The Strapping System 1550 is coupled to the bladder envelope and adapted to secure the bladder envelope in a fitted position adjacent to the knee therapy site. The thermal exchange Bladder 1700 may have a concave inner contour adapted to fit the shape of the knee therapy site. The bladder envelope is flexibly configured to take on the shape of the thermal exchange bladder. Therefore, the Thermal Exchange Layer 901 may closely contact a substantial portion of the knee therapy site. The Strapping System 1550 is configured to enhance the contact between the bladder envelope and the knee therapy site, facilitating optimal thermal transfer between the Thermal Exchange Layer 901 and the therapy site. In the pictured embodiment, the Strapping System 1550 includes upper and lower pairs of straps indicated at 1550*a*, 1550*b* and 1550*c*, 1550*d* respectively. Each said strap may be affixed to said First Face 1630 of the bladder envelope as shown at 1550*a*, 1550*b*, 1550*c*, and 1550*d*. The upper and lower pairs of straps may be selectively tightened and loosened while the Thermal Exchange Layer 901 is in a generally fitted position, to customize a particular therapy and achieve a better fit. The straps are positioned so as to provide a mechanism for adjusting the tension of the Strapping System 1550 from the perimeter of the bladder envelope, which effectively pulls the envelope around the knee therapy site to enhance contact of the therapy site with the Thermal Exchange Layer 901. Therefore, the Strapping System 1550 improves the fit and the compression of the Thermal Exchange Layer 901.

Strapping systems may include releasable hook and/or loop material, which may be selectively attached to complementary hook and/or loop material. For example, loop material of Second Face 1530 and Hook Material 1650 of Strapping System 1550 may be adapted to releasably secure a portion of the Strapping System 1550 to a portion of the bladder envelope. Some portions of the Strapping System 1550 may be adapted to secure to other portions of the Strapping System 1550. Strapping Systems 1550 may be configured in a variety of arrangements for providing desired support. The Strapping Systems 1530 may include buckles, slides, compression fasteners, and/or other means for customizing the strapping system's ability to position and secure a bladder envelope and/or thermal exchange Bladder 1700.

The Strapping System 1550 may be used in conjunction with the Knee Brace 1200. The strapping system may act in cooperation with the active thermal exchange Bladder 1700 of the instant invention to hold the Thermal Exchange Layer 901 in close contact with the therapy site during the application of thermal therapy while the therapy site is engaged in the Knee Brace 1200. Once the Thermal Exchange Layer 901 is secured in place, the strain relieving aspects of the instant Bladder 1700 allow the application of thermal therapy while the knee is flexed and extended as the therapy recipient moves within the configured angle of flexion defined by the Knee Brace 1200.

Alternatively, the Strapping System 1550 may be used in conjunction with the CPM Device 1300. The strapping system may act in cooperation with the active thermal exchange Bladder 1700 of the instant invention to hold the Thermal Exchange Layer 901 in close contact with the therapy site during the application of thermal therapy while the therapy site is articulated passively by the CPM Device 1300. Once the Thermal Exchange Layer 901 is secured in place, the strain relieving aspects of the instant Bladder 1700 allow the application of thermal therapy while the knee is flexed and extended by the CPM Device 1300.

FIG. 17 is a top plan view of an active thermal exchange Bladder 1700 of a knee Thermal Exchange Layer 901 adapted for use with the Knee Brace 1200 and/or Continuous Passive Motion Device 1300 in accordance with an embodiment of the present invention. The instant Thermal Exchange Layer 901 may also be used in active motion therapy, as well as static thermal therapy. The thermal exchange Bladder 1700 has an outer perimeter. The outer perimeter is defined by exterior perimeter portions 1730a, 1730b, 1730c, 1730d, 1730e and 1730f and indentations 1710a and 1710b. As shown, indentations 1710a and 1710b are respectively defined by rectilinear perimeter portions 1740a and 1740b, and 1740c and 1740d. It should be understood that the illustrated embodiment is provided as an example, and the thermal exchange bladders may have perimeters with different shapes, including more or fewer indentations, which may be configured differently than those shown in FIG. 17. As shown, indentations 1710a and 1710b are open, meaning that there is relatively more space between perimeter portions 1740a and 1740b, and 1740c and 1740d, than there would be in a closed configuration. In some embodiments, the perimeter may be completely closed, meaning that there is substantially no space between perimeter portions 1740a and 1740b, and 1740c and 1740d, thus effectively positioning perimeter portions 1740a and 1740b, and 1740c and 1740d as substantially uninterrupted continuous perimeter portions.

The active exchange thermal Bladder 1700 of FIG. 17 also includes Strain Relief Darts 1720a and 1720b. The instant Strain Relief Darts 1720 incorporated into the design of the Bladder 1700 allow for continuous application of thermal or contrast therapy during flexure of the knee. Indentations 1710a and 1710b are substantially v-shaped. For instance, Indentations 1710a is defined by rectilinear perimeter portions 1740a and 1740b which extend from perimeter portions 1730a and 1730b, respectively, towards the Strain Relief Dart 1720a located at the apex of the v-shaped Indentation 1710a. Said Strain Relief Dart 1720a is substantially curvilinear and acts to prevent bunching of material at the apex of the Indentation 1710a while the knee is in flexure. Resultantly, it is possible to deliver thermal and compressive therapy to the knee while the knee is being articulated through a therapeutic range of motion by a suitable CPM Device 1300.

Strain relief darts 1720a and 1720b are advantageously located at critical sites within the knee Thermal Exchange Layer 901. Articulation of the knee, whether done actively or through the use of a CPM Device 1300, necessitates the flexure of the active thermal exchange bladder along a central axis connecting Indentations 1710a and 1710b. As a result, the end points of said central axis are sites critical to the ability of the bladder to flex and extend with the articulation of the shoulder. Strain Relief Darts 1720a and 1720b are strategically located at said critical sites in order to minimize the strain along said axis. By relieving bunching or kinking at the critical sites, Strain Relief Darts 1720a and 1720b enable the effective use of thermal and compressive therapy during flexure of the therapy site.

The active thermal exchange Bladder 1700 depicted in FIG. 17 includes a matrix of Intermittent Welds indicated generally at 1750. In addition to the novel Strain Relief Darts 1720, the instant Thermal Exchange Layers 901 incorporate a novel weld matrix which optimizes the distribution of fluid circulated in the bladder during therapy. Each of the plurality of Intermittent Welds indicated at 1750 is spaced along the matrix at a position which is equidistant from each other such weld. The matrix design evenly spaces the plurality of Welds 1750 within the matrix. The matrix is defined independently of the shape of the bladder into which it is to be incorporated. The pre-defined spacing is maintained as the faces of the Bladder 1700 are welded together at each of the Intermittent Weld Welds 1750. The equidistant nature of each Weld 1750 is maintained regardless of where the Perimeter 1740 of the Bladder 1700 intersects the pre-defined matrix. As such, Welds 1750 may blend into the edges of the bladder as shown in FIG. 17.

The instant weld matrix has been found to help optimize the distribution of fluid, pressure and temperature throughout the Bladder 1700. The even temperature distribution gives the advantage of even application of thermal or contrast therapy at the knee therapy site. The even distribution of pressure throughout the Bladder 1700 aids in the application of constant compression at the knee therapy site. This feature is especially important when the Thermal Exchange Layer 901 is to be used in conjunction with a CPM Device 1300, or in conjunction with any form of active or passive motion at the knee therapy site. As noted above, known Thermal Exchange Layers 901 have a tendency to bunch and kink at critical sites in flexure. When under fluid pressure during the application of thermal therapy, the Bladder 1700 tends to offer even more resistance to motion at these critical sites. The instant weld matrix configuration evenly distributes pressure throughout the Bladder 1700 allowing the Bladder 1700 to flex and extend more easily while delivering thermal and compressive therapy.

By optimizing the distribution of fluid pressure in the Bladder 1700, the instant Thermal Exchange Layer 901 minimizes resistance to motion throughout the Thermal Exchange Layer 901. In order to articulate a therapy site through a selected range of motion while offering continuous application of thermal therapy, the Thermal Exchange Layer 901 may flex and extend along with the therapy site. While the instant Thermal Exchange Layers 901 eliminate bunching or kinking at critical sites, pressurized Bladders 1700 intrinsically offer resistance to motion. Internal bladder pressure exerts an outward force on the faces of the Bladder 1700 which must be overcome by an external force in order to move the Bladder 1700 through the desired range of motion. By evenly distributing the fluid and, by extension, the pressure throughout the Bladder 1700, the instant design minimizes the resistance of the Bladder 1700 to motion.

As shown in FIG. 16, a thermal exchange Bladder 1700 is generally flat when it is in an open configuration, although the thermal exchange Bladder 1700 may be made from a flexible material, which allows the Bladder 1700 to be temporarily bent or otherwise flexed from a flat shape. In other words, in an open configuration the thermal exchange Bladder 1700 is not predisposed to have a concave shape, or similar three-dimensional shape. In a closed position the thermal exchange Bladders 1700 have concave inner contours, which are shaped to fit knee, shoulder, jaw, chest and other therapy sites. Indentations 1710 of the Thermal Exchange Layers 901 may be fixed in a closed position, giving the thermal exchange Bladders 1700 a permanent concave inner contour. The Indentations 1710 may be fixed by stitching, gluing, welding, or similar fastening means. In some embodiments, the Indentations 1710 may be molded together, and in some embodiments, the Bladder 1700 may be directly molded with a concave inner contour.

Shaping the thermal exchange Bladder 1700 with a concave inner contour adapted to closely correspond to a particular therapy site increases the contact between the Thermal Exchange Layer 901 and the therapy site, which may increase the effectiveness of applied therapies. Furthermore, fixing a Bladder 1700 in a predefined shape helps ensure that the Thermal Exchange Layer 901 is correctly positioned to further improve applied therapies. The thermal exchange Bladder 1700 may be constructed from flexible materials that allow the Bladder 1700 to flex from a predefined contoured shape to more closely correspond to a particular therapy site, such as when a Strapping System 1550 is tightened to secure the Thermal Exchange Layer 901 adjacent the therapy site.

Using closed Indentations 1710 as a means for forming concave inner contours provides a great deal of design freedom, while limiting the cost of manufacturing the Bladders 1700. Indentations 1710 with different sizes, and shapes, as well as different positioning, facilitate forming bladders with virtually any predefined shape. The Bladders 1700 may be manufactured flat, which limits costs. After flat Bladders 1700 are formed, the indentations may be closed, thus giving the Bladders 1700 a predefined contour.

Additionally, the system may incorporate the use of a CPM Device 1300 to passively articulate the therapy site through a therapeutic range of motion. As discussed above, passive or active motion of a therapy site is often indicated for more effective therapy. Heretofore, therapy pads had not been adapted to allow for articulation of the therapy site with effective application of thermal therapy. The Bladders 1700 of the instant invention have been adapted to allow for continuous thermal therapy and constant compression in flexure.

Alternate Therapeutic Knee Brace System with Continuous Passive Motion Designs FIG. 18 is an isometric view of a therapeutic Knee Brace 1200 coupled with a Continuous Passive Motion Device 1300 in accordance with an embodiment of the present invention. The purpose of this illustration is to accentuate alternate embodiments of the CPM Device 1300. In the present embodiment, in addition to the Pivoting Arms 1831, there are Cross Arms 1830 that are capable of pivoting at Pivoting Points 1835. The Cross Arms 1830 couple at the Pivoting Points 1835 to the Pivoting Arms 1831. In such an embodiment the Yoke 1832 may be stationary, and the power source may act upon a single Pivoting Arm 1831 in order to effectuate a flexion of the Knee Brace 1200. Movement of the Pivoting Arms 1831 results in moving of the Cross Arms 1830. Such movement results in a flexion of the Knee Brace 1200.

Such a system requires less mechanical complexity than the previous embodiments; however maintenance of the rotational hip axis in a stationary position may be less effectuated under the present embodiment than previous embodiments due to inconsistencies in the length of the therapy recipients' legs.

FIG. 19 is an isometric view of a Continuous Passive Motion System 1900 in accordance with an embodiment of the present invention. The purpose of this illustration is to show a CPM System 1900 capable of thermal contrast therapy without the utilization of a Knee Brace 1200. Such a CPM System 1900 may include a Base 1933 for structural support. The Base 1933 may house the Contrast Therapy System 10 for supplying therapy fluid to the Thermal Exchange Layer 901. Additionally, the Base 1933 may house a power source for moving Pivotal Arms 1931 of the CPM System 1900. In addition to the Pivoting Arms 1931 there are Cross Arms 1930 that are capable of pivoting at Pivoting Points 1935. The Cross Arms 1930 couple at the Pivoting Points 1935 to the Pivoting Arms 1931. In such an embodiment the Yoke 1932 may be stationary, and the power source may act upon a single Pivoting Arm 1931 in order to effectuate a flexion of the Cradle Struts 1934. Movement of the Pivoting Arms 1931 results in moving of the Cross Arms 1930. Such movement results in a flexion of the Cradle Struts 1934 along Pivoting Points 1935. Strung between the Cradle Struts 1934 are Leg Cradles 1932 designed to support the therapy recipient's leg during CPM therapy. Leg Cradles 1932 may be cloth, contoured plastic or metal, or any other suitable material. Additionally, Leg Cradles 1932 may circumvent the wearer's leg. A Foot Rest 1936 is illustrated coupled to the Cradle Struts 1934 to provide lower leg and foot support.

The Thermal Exchange Layer 901 may be utilized with the CPM system 1900 to provide thermal contrast therapy simultaneously with continuous passive motion therapy. Of course additional alternate embodiments of the CPM System 1900 may be utilized in conjunction with a thermal contrast system.

Method of Administering Contrast of Thermal Therapy

FIG. 20 shows, generally at 2000, a method of administering contrast therapy to a therapy recipient. Method 2000 includes, at 2001, providing a volume of a relatively hot fluid. As explained above, a fluid may be received by a hot reservoir, where it may be heated by a heater. The relatively hot fluid may be virtually any temperature, with temperatures of approximately 100 to 105 degrees Fahrenheit being suitable for many applications. The method further includes, at 2002, providing a volume of a relatively cold fluid. Fluid may be received by a cold reservoir, where it may be cooled. In some embodiments, ice slurry is used to cool fluid passing through the cold reservoir, and in some embodiments a cooler is used. The cold fluid may be virtually any temperature (cooler than the hot fluid), with temperatures of approximately 32 to 45 degrees Fahrenheit being suitable for many applications.

At 2003, the method includes selecting relative amounts of the hot and cold fluids to mix as a therapy fluid with a desired initial therapy temperature. A mixture of hot and cold fluids with a specific ratio may be selected with a mixing valve, or similar mechanism, that is configured to receive the hot and cold fluids, and pass the mixture of the hot and cold fluids as a therapy fluid. The ratio of hot to cold fluid in the therapy fluid may range from 100% hot fluid to 100% cold fluid, as well as any intermediate ratio. The temperature of the therapy fluid corresponds to the ratio of hot and cold fluids mixed, with greater percentages of hot fluid resulting in higher temperatures, and greater percentages of cold fluid resulting in cooler temperatures. The therapy fluid's maximum temperature is approximately the temperature of the hot fluid, and is achieved by selecting a ratio of all hot fluid and no cold fluid. Similarly, the therapy fluid's minimum temperature is approximately the temperature of the cold fluid, and is achieved by selecting a ratio of all cold fluid and no hot fluid.

As shown at 2004, the method further includes circulating the therapy fluid with the initial therapy temperature through a Therapy Pad 22, which includes the Thermal Exchange Layer 901 of the present invention. The therapy fluid may be circulated in a pulsing stream, so as to impart a vibration that is useful in providing a therapeutic massage. Of course, the flow may instead be smooth. At 2005, the method includes applying the Therapy Pad 22, here a Thermal Exchange Layer 901, to the therapy recipient. This may be performed by donning the Therapeutic Knee Brace and Continuous Passive Motion Device Assembly 902. The Therapeutic Knee Brace and Continuous Passive Motion Device Assembly 902 additionally supplies knee support, and therapy site compression, which may aid in the overall therapy. The temperature of the therapy fluid may be translated through the Therapy Pad 22, here a Thermal Exchange Layer 901, to the therapy recipient. For example, if the initial temperature of the therapy fluid is relatively hot, for instance 105 degrees Fahrenheit, the Thermal Exchange Layer 901 may be used to heat a therapy site on the therapy recipient. Similarly, a therapy fluid with a relatively cold therapy temperature, such as 40 degrees Fahrenheit, may be used to cool a therapy site.

The method further includes, at 2005, returning the therapy fluid to at least one of the volume of hot fluid and the volume of cold fluid. Returning the therapy fluid to either or both of the volumes of hot and cold fluids allows the therapy fluid to be recycled. The returned therapy fluid may then be heated and/or cooled, and eventually may be recirculated to the Therapy Pad 22, here the Thermal Exchange Layer 901. In this manner, a limited volume of fluid in a system may be used to provide an ongoing therapy. The fluid may be repeatedly heated and/or cooled, and thus the character of the treatment may be continually changed.

As shown at 2006, the method may also include selecting relative amounts of the hot and cold fluids to mix as a therapy fluid with a desired contrast therapy temperature different than the initial therapy temperature. By changing the relative amounts of hot and cold fluids, the resulting temperature of the therapy fluid may be changed, which changes the therapy received by the therapy recipient. It is within the scope of the invention to make such temperature changes quickly, such as in under a minute, which may result in an average temperature change greater than 1 degree Fahrenheit per second. At 2007, the method may further include circulating the therapy fluid with the contrast therapy temperature through the Therapy Pad 22, here the Thermal Exchange Layer 901. Circulating the therapy fluid with the contrast therapy temperature allows the therapy recipient to experience a cold treatment immediately after a hot treatment or a hot treatment immediately after a cold treatment. It should be understood that the period of change between respective treatments is ideally very small, such as under one minute. This process may be repeated one or more times, and each time the relative amounts of hot and cold fluids may be selected to result in a desired therapy temperature.

The present invention can also be practiced with other techniques for providing thermal or contrast therapy to a therapy recipient and knee support. For example, it is possible, using the Therapeutic Knee Brace and Continuous Passive Motion Device Assembly 902 of the instant invention, to be configured to incorporate massage pads for massage therapy at the therapy site as well.

In sum, the present invention provides a leg brace which is detachable from the CPM device and integrates a thermal exchange layer, thereby providing the ability to seamlessly transition from normal activity to CPM therapy without removing the brace. The advantages of such a cost-effective and efficient detachable system include ease of use, reduced pain by the wearer, shorter preparation time for CPM therapy, enhanced support of the knee joint during CPM therapy, ease of cleaning, and ability to share the CPM device among different therapy recipients in an institutional or outpatient environment.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A therapeutic knee brace system useful in association with a knee joint therapy recipient, a thermal contrast therapy system and a continuous passive motion (CPM) device, the therapeutic knee brace system comprising:
    a leg brace configured to support a leg of the therapy recipient, wherein the leg brace includes a left lower bracing member, a right lower bracing member, a left upper bracing member and a right upper bracing member, wherein the right lower bracing member couples to the right upper bracing member via a right brace joint, and the left lower bracing member couples to the left upper bracing member via a left brace joint, further wherein the angle of flexion of at least one of the right and left brace joint is configurable by the therapy recipient, and wherein each of the left lower bracing member, the right lower bracing member, the left upper bracing member and the right upper bracing member are each configured to detachably couple to a single corresponding arm of a continuous passive motion device via a pin and slot, and wherein the therapeutic knee brace system communicates with the CPM device, and wherein the communication includes dynamic transmission of the angle of flexion and range of flexion, and wherein the communication may be mechanical, electrical or wireless, and wherein the leg brace includes at least one retainer for securing the leg of the therapy recipient to the leg brace; and
    an active thermal exchange bladder configured to fit the knee joint of the therapy recipient, and wherein the active thermal exchange bladder is coupled to a thermal contrast therapy system that delivers a thermal therapy fluid to the thermal exchange bladder, and wherein the active thermal exchange bladder includes a strain relief dart which reduces bunching of the active thermal exchange bladder as the therapy recipient's knee joint is bent within the range of flexion.

2. The therapeutic knee brace system of claim 1, wherein the angle of flexion is selectable by the therapy recipient.

3. The therapeutic knee brace system of claim 1, wherein the active thermal exchange bladder may be coupled to the leg brace using a strapping system.

4. The therapeutic knee brace system of claim 1, wherein the thermal contrast therapy system includes a hot reservoir for holding a relatively hot fluid, a cold reservoir for holding a relatively cold fluid, a mixing valve for receiving a selected ratio of the hot and cold fluids from the hot and cold reservoirs to generate the therapy fluid, a pump for pumping the therapy fluid, and operable to deliver the therapy fluid with a therapy temperature determined by the selected ratio.

5. The therapeutic knee brace system of claim 4, wherein the thermal exchange bladder provides compression on the knee joint of the therapy recipient, wherein the compression is generated by pressure within the thermal exchange bladder, and wherein the pressure is regulated by the pump of the thermal contrast therapy system.

6. The therapeutic knee brace system of claim 4, wherein the pump causes constant pressure within the thermal exchange bladder, wherein the constant pressure produces steady compression on the knee joint of the therapy recipient.

7. The therapeutic knee brace system of claim 4, wherein the pump causes dynamic pressure within the thermal exchange bladder, wherein the dynamic pressure produces pulsating compression on the knee joint of the therapy recipient.

8. The therapeutic knee brace system of claim 1, wherein the knee brace coupler is configured to enable the CPM device to be capable of functioning, including being configured to enable manipulating the therapeutic knee brace system when the therapeutic knee brace system is coupled to the CPM device.

* * * * *